United States Patent
DeCarbo et al.

(10) Patent No.: US 11,622,797 B2
(45) Date of Patent: Apr. 11, 2023

(54) METATARSOPHALANGEAL JOINT PREPARATION AND METATARSAL REALIGNMENT FOR FUSION

(71) Applicant: Treace Medical Concepts, Inc., Ponte Vedra, FL (US)

(72) Inventors: William T. DeCarbo, Pittsburgh, PA (US); Paul Dayton, Fort Dodge, IA (US); W. Bret Smith, Lexington, SC (US); Robert D. Santrock, Morgantown, WV (US); Daniel J. Hatch, Greeley, CO (US); Jody McAleer, Jefferson City, MO (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 254 days.

(21) Appl. No.: 17/163,120

(22) Filed: Jan. 29, 2021

(65) Prior Publication Data
US 2021/0236180 A1  Aug. 5, 2021

Related U.S. Application Data

(60) Provisional application No. 62/968,244, filed on Jan. 31, 2020.

(51) Int. Cl.
  *A61B 17/72* (2006.01)
  *A61B 17/00* (2006.01)
  *A61B 17/68* (2006.01)

(52) U.S. Cl.
  CPC ............... *A61B 17/7291* (2013.01); *A61B 2017/00407* (2013.01); *A61B 2017/681* (2013.01)

(58) Field of Classification Search
  CPC ...... A61B 17/7291; A61B 2017/00407; A61B 2017/681; A61B 17/66; A61B 17/68
  (Continued)

(56) References Cited

U.S. PATENT DOCUMENTS

| 3,664,022 A | 5/1972 | Small |
| 4,069,824 A | 1/1978 | Weinstock |

(Continued)

FOREIGN PATENT DOCUMENTS

| AU | 2009227957 B2 | 7/2014 |
| CA | 2491824 A1 | 9/2005 |

(Continued)

OTHER PUBLICATIONS

"Accu-Cut Osteotomy Guide System," BioPro, Brochure, Oct. 2018, 2 pages.

(Continued)

*Primary Examiner* — Eduardo C Robert
*Assistant Examiner* — Christina Negrellirodriguez
(74) *Attorney, Agent, or Firm* — Fredrikson & Byron, P.A.

(57) ABSTRACT

A method of preparing a metatarsophalangeal joint for fusion may involve surgically accessing the metatarsophalangeal joint and separating the metatarsal from the opposed proximal phalanx at the joint. The technique may involve preparing an end of the metatarsal and preparing an end of the opposed proximal phalanx for fusion. With or without the aid of a bone positioner, the metatarsal may be moved in one or more planes, such as the frontal and transverse planes. The proximal phalanx may also be moved in one or more planes, for example relative to the moved metatarsal. Subsequently, a bone fixation device can be applied across or through the metatarsophalangeal joint separating the metatarsal from the opposed proximal phalanx.

25 Claims, 19 Drawing Sheets

(58) Field of Classification Search
USPC .......................................................... 606/62
See application file for complete search history.

(56) References Cited

U.S. PATENT DOCUMENTS

| | | | |
|---|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clybum |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 6,964,645 B1 | 11/2005 | Smits |
| 7,018,383 B2 | 3/2006 | McGuire |
| 7,033,361 B2 | 4/2006 | Collazo |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,241,298 B2 | 7/2007 | Nemec et al. |
| 7,282,054 B2 | 10/2007 | Steflensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,518,045 B2 | 8/2013 | Szanto |

(56) References Cited

U.S. PATENT DOCUMENTS

| | | |
|---|---|---|
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Haddad et al. |
| 9,592,084 B2 | 3/2017 | Grant |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,779,867 B2 | 9/2020 | Penzimer et al. |
| 10,939,939 B1 | 3/2021 | Gil et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde, Jr. |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1* | 1/2007 | Stone .................. A61B 17/683 606/90 |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Fyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |

(56) References Cited

U.S. PATENT DOCUMENTS

| | | |
|---|---|---|
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0230843 A1 | 8/2015 | Palmer et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0290614 A1 | 10/2017 | Weiner et al. |
| 2018/0021145 A1 | 1/2018 | Seavey et al. |
| 2018/0132868 A1 | 5/2018 | Dacosta et al. |
| 2018/0235765 A1 | 8/2018 | Welker et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | 2004174265 A | 6/2004 |
| JP | 2006158972 A | 6/2006 |
| JP | 4134243 B2 | 8/2008 |
| JP | 4162380 B2 | 10/2008 |

(56) References Cited

FOREIGN PATENT DOCUMENTS

| | | |
|---|---|---|
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

"Acumed Osteotomiesystem Operationstechnik," Acumed, 2014, 19 pages (including 3 pages English translation).

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented STAR Total Ankle Prostheses," The Journal of Bone and Joint Surgery, vol. 86(1, Suppl 2), Sep. 2004, pp. 103-111, (Abstract Only).

Bednarz et al., "Modified Lapidus Procedure for the Treatment of Hypermobile Hallux Valgus," Foot & Ankle International, vol. 21, No. 10, Oct. 2000, pp. 816-821.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal To Proximal Articular Set Angle and Hallux Alignment in Patients Undergoing Tarsometatarsal Arthrodesis For Hallux Abducto Valgus: A Case Series And Critical Review of The Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Bofeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.

"Futura Forefoot Implant Arthroplasty Products," Tornier, Inc., 2008, 14 pages.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fur die Knieendoprothetik," Forschungsberichte, Technische Universitat Munchen, 165, 2002, 11 pages, including partial English Translation.

Gregg et al., "Plantar plate repair and Weil osteotomy for metatarsophalangeal joint instability," Foot and Ankle Surgery, vol. 13, 2007, pp. 116-121.

Grondal et al., "A Guide Plate for Accurate Positioning of First Metatarsophalangeal Joint during Fusion," Operative Orthopadie Und Traumatologie, vol. 16, No. 2, 2004, pp. 167-178 (Abstract Only).

"HAT-TRICK Lesser Toe Repair System," Smith & Nephew, Brochure, Aug. 2014, 12 pages.

"HAT-TRICK Lesser Toe Repair System, Foot and Ankle Technique Guide, Metatarsal Shortening Osteotomy Surgical Technique," Smith & Nephew, 2014, 16 pages.

Hetherington et al., "Evaluation of surgical experience and the use of an osteotomy guide on the apical angle of an Austin osteotomy," The Foot, vol. 18, 2008, pp. 159-164.

(56) References Cited

OTHER PUBLICATIONS

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Kim et al., "A New Measure of Tibial Sesamoid Position in Hallux Valgus in Relation to the Coronal Rotation of the First Metatarsal in Ct Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopadie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopadie und Traumatologie, vol. 22, No. 1, 2010, pp. 63-80, including English Abstract on p. 64.
Magin, "Die belastungsstabile Lapidus-Arthrodese bei Hallux-valgus-Deformitat mittels IVP-Plallenfixateur (V-TEK-System)," Operative Orthopadie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98,2012, pp. 677-683.
Hatch etal, "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Ray et al., "Hallux Valgus," Foot & Ankle Orthopaedics, vol. 4, No. 2, 2019, pp. 1-12.
Santrock et al., "Hallux Valgus Deformity and Treatment: A Three-Dimensional Approach: Lapiplasty," Foot & Ankle Clinics, vol. 23, No. 2, 2018, pp. 281-295.

Ray et al., "Multicenter Eady Radiographic Outcomes of Triplanar Tarsometatarsal Arthrodesis With Eady Weightbearing," Foot & Ankle International, vol. 40, No. 8, 2019, pp. 955-960.
Smith et al., "Intraoperative Multiplanar Alignment System to Guide Triplanar Correction of Hallux Valgus Deformity," Techniques in Foot & Ankle Surgery, 2017, 8 pages.
Smith et al., "Understanding Frontal Plane Correction in Hallux Valgus Repair," Clinics in Podiatric Medicine and Surgery, vol. 35,2018, pp. 27-36.
International Patent Application No. PCT/US2021/015883, International Search Report and Written Opinion dated May 21, 2021, 9 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," clinical Orthopaedics and Related Research, vol. 151, Sep. 1980, pp. 244-255.
Siddiqui et al. "Fixation of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.

(56) References Cited

OTHER PUBLICATIONS

Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fu chirurgie Das V-tek-System," ABW Wissenschaftsverlag GmbH, 2009, 11 pages, including English Abstract.
Weber et al., "A Simple System For Navigation of Bone Alignment Osteotomies of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online Dec. 26, 2019, pp. 426-436.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.

Ray et al., "Multicenter Early Radiographic Outcomes of Triplanar Tarsometatarsal Arthrodesis With Eady Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Septembers, 2019, pp. 641-648.
Dayton et al., "Comparison of Radiographic Measurements Before and After Triplane Tarsometatarsal Arthrodesis tor Hallux Valgus," The Journal of Foot & Ankle Surgery, vol. 59, 2020, pp. 291-297.
Dayton et al., "Evidence-Based Bunion Surgery: A Critical Examination of Current and Emerging Concepts and Techniques," Springer International Publishing, 2017, 254 pages.
Dayton et al., "Comparison of Tibial Sesamoid Position on Anteroposterior and Axial Radiographs Before and After Triplane Tarsal Metatarsal Joint Arthrodesis," The Journal of Foot & Ankle Surgery, vol. 56, 2017, pp. 1041-1046.
Dayton et al., "Biomechanical Characteristics of Biplane Multiplanar Tension-Side Fixation for Lapidus Fusion," The Journal of Foot & Ankle Surgery, vol. 57,2018, pp. 761-765.
Dayton et al., "Progression of Healing on Serial Radiographs Following First Ray Adhrodesis in the Foot Using a Biplanar Plating Technique Without Compression," The Journal of Foot & Ankle Surgery, 2018, 7 pages.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Aiyer et al., "Prevalence of Metatarsus Adductus in Patients Undergoing Hallux Valgus Surgery," Foot & Ankle International, vol. 35, No. 12, 2014, pp. 1292-1297.
Bennett et al., "Intraosseous Sliding Plate Fixation Used in Double Osteotomy Bunionectomy," Foot & Ankle International, vol. 40, No. 1, 2019, pp. 85-88.
Buda et al., "Effect of Fixation Type and Bone Graft on Tarsometatarsal Fusion," Foot & Ankle International, vol. 39, No 12, 2018, pp. 1394-1402.
Chomej et al., "Lateralising DMMO (MIS) for simultaneous correction of a pes adductus during surgical treatment of a hallux valgus," The Foot, vol. 45, Dec. 2020, 33 pages.
Cichero et al., "Different fixation constructs and the risk of non-union following first metatarsophalangeal joint arthrodesis," Foot and Ankle Surgery, vol. 27, 2021, pp. 789-792.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
DeHeer et al., "Procedure-Specific Hardware Removal After Evans Osteotomy," Journal of the American Podiatric Medical Association, vol. 110, No. 2, Mar./Apr. 2020, 7 pages.
Fazal et al., "First metatarsophalangeal joint arthrodesis with two orthogonal two hole plates," Acta Orthopaedica et Fraumatologica Turcica, vol. 52, 2018, pp. 363-366.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fraissler et al., "Treatment of hallux valgus deformity," Efort Open Reviews, vol. 1, Aug. 2016, pp. 295-302.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Guitteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic anti Trauma Surgery, vol. 133, 2013, pp. 753-755.

(56) References Cited

OTHER PUBLICATIONS

Ho et al., "Hallux rigidus," Efort Open Reviews, vol. 2, Jan. 2017, pp. 13-20.
Hunt et al., "Locked Versus Nonlocked Plate Fixation For Hallux MTP Arthrodesis," Foot and Ankle International, vol. 32, No. 7, Jul. 2011, pp. 704-709.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Kurup et al., "Midfoot arthritis- current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
Machacek Jr. et al., "Salvage of a Failed Keller Resection Arthroplasty," The Journal of Bone and Joint Surgery, vol. 36A, No. 6, Jun. 2004, pp. 1131-1138.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.
McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Nix et al., "Prevalence of hallux valgus in the general population: a systematic review and meta-analysis," Journal of Foot and Ankle Research, vol. 3, No. 21, 2010, 9 pages.
Park et al., "Comparative analysis of clinical outcomes of fixed-angle versus variable-angle locking compression plate tor the treatment of Lisfranc injuries," Foot and Ankle Surgery, vol. 26, 2020, pp. 338-342.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Shima et al., "Operative Treatment for Hallux Valgus With Moderate to Severe Metatarsus Adductus," Foot & Ankle International, vol. 40, No. 6, 2019, pp. 641-647.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Williams et al., "Metatarsus adductus: Development of a non-surgical treatment pathway," Journal of Paediatrics and Child Health, vol. 49, 2013, pp. E428-E433.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.

(56) References Cited

OTHER PUBLICATIONS

Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664 670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," Bsued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube com/watch?v=jqJyE/pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
<https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.nmpglobal-learhmpgloballe.com/site/podipodi/article/5542>, dated May 2006, 8 pages.

(56) References Cited

OTHER PUBLICATIONS

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al, "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., U.S. Provisional Application Entitled Indexed Tri-Planar Osteotomy Guide and Method, U.S. Appl. No. 62/118,378, filed Feb. 19, 2015, 62 pages.
Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthpaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Quix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," UFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus," The Foot and Ankle, Second Edition, Chapter 8, 2002, pp. 99-117.
Sokoloff, "Lapidus Proceudre," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

\* cited by examiner

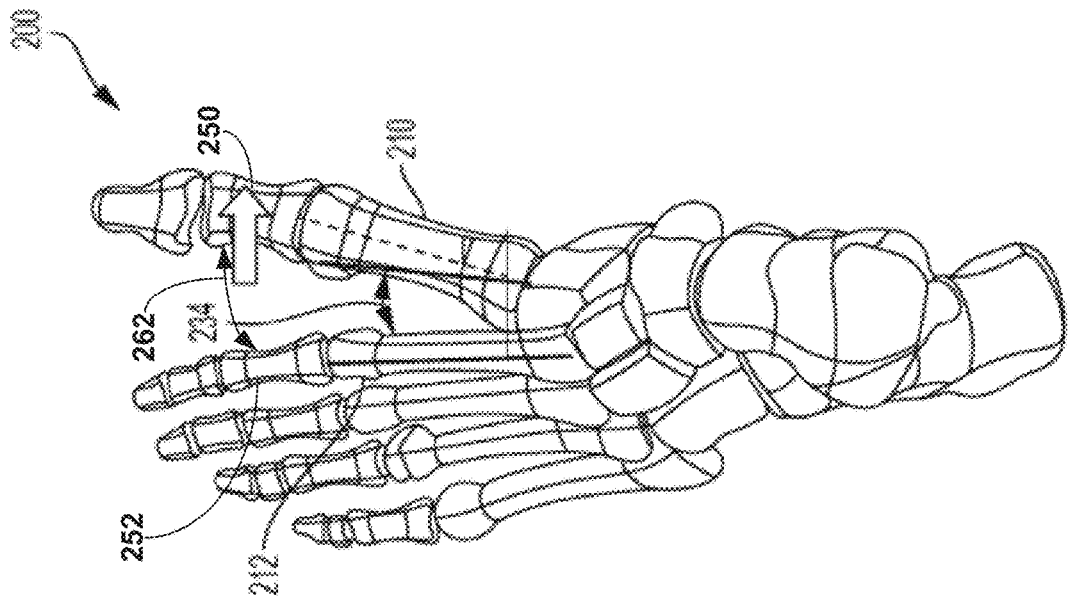

METATARSOPHALANGEAL JOINT PREPARATION AND METATARSAL REALIGNMENT FOR FUSION

RELATED MATTERS

This application claims the benefit of U.S. Provisional Patent Application No. 62/968,244, filed Jan. 31, 2020, the entire contents of which are incorporated herein by reference.

TECHNICAL FIELD

This disclosure relates to devices and techniques for metatarsophalangeal joint preparation and metatarsal realignment.

BACKGROUND

The human foot includes the five toes (which are also known as the "phalanges") and their connecting long bones (or "metatarsals"). The joint between a metatarsal and a phalange is called the metatarsophalangeal ("MTP") joint. Several small bones together comprise a phalanx or toe. Four of the five toes have three phalanx bones respectively connected by two joints. The big toe (or "*hallux*") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The two sesamoid bones are located underneath the first metatarsal bone and assist in flexion of the big toe at the first MTP joint.

*Hallux rigidus* is a degenerative disease of the first metatarsophalangeal joint. It is the most common form of arthritis in the foot, reportedly affecting 1 in 40 people over the age of 50. The first MTP joint plays an important functional role during the gait cycle as it carries a significant amount of an individual's body weight with each step. Osteophyte formation and degeneration of the cartilage occurs dorsally in early stages of the disease and progresses to involve the entire first MTP joint. Consequently, individuals with *Hallux rigidus* experience joint pain and decreased range of motion in the sagittal plane. This leads to altered gait mechanics and significant reduction in activity and quality of life for patients.

SUMMARY

In general, this disclosure is directed to devices and techniques for preparing the metatarsophalangeal ("MTP") joint for fusion and realigning the metatarsal and phalanx separated by the joint. In some implementations, a clinician surgically accesses the MTP joint and separates the metatarsal from the opposed phalanx for subsequent bone preparation and realignment. The clinician may make a longitudinal incision, e.g., just medial to the extensor hallucis longus tendon. With the MTP joint exposed, the clinician may separate the end face of the metatarsal from the end face of the opposed phalanx to provide working space. The clinician may subsequently prepare the end face of the metatarsal and the end face of the opposed phalanx for fusion. Example preparation steps may include reaming, cutting, rongeuring, curetting, burring, fenstrating and/or other similar techniques for exposing subchondral bone and/or establishing bleeding bone faces to promote fusion following rejoining of the metatarsal and phalanx.

Either before or after preparation of one or both end faces, the metatarsal is realigned within one or more planes in three-dimensional space. In one example, the clinician engages a bone positioner with the metatarsal and a bone other than the metatarsal. The bone positioner can then be actuated to move the metatarsal in one or more planes for realignment. The use of the bone positioner can provide an instrumented approach to metatarsal realignment that allows for repeatable, consistent clinical outcomes patient-to-patient and clinician-to-clinician. In other examples, however, the clinician may realign the metatarsal manually without the aid of an instrumented bone positioner bridging between the metatarsal and another anchoring bone. The clinician may realign the metatarsal in one or more planes at a time, e.g., including the frontal plane.

Independent of the specific technique the clinician uses to realign the metatarsal, the clinician may also realign the proximal phalanx relative to the metatarsal. As one realignment, the clinician may adjust the orientation of the phalanx in the sagittal plane to help set a desired amount of dorsiflexion. As another example realignment, the clinician may rotate the phalanx within the frontal plane to help provide anatomically accurate positioning of the plantar side of the phalanx in the frontal plane.

To help guide accurate realignment and visualization of the proximal phalanx, the clinician may provisionally fixate the phalanx to an adjacent bone during and/or after realignment. For example, the clinician may insert a pin (e.g., a Kirschner wire, which is also referred to as a K wire) through the distal end of the phalanges and advance the pin proximally toward the metatarsal.

In the case of the first metatarsal, for instance, the clinician can insert the pin through the distal phalanx followed by the proximal phalanx and then lodge the distal portion of the pin in the first metatarsal. The pin can project distally out of the distal phalanx, providing a visible axis of rotation for realigning the proximal phalanx in the frontal plane. When so implemented, the clinician may first set the orientation of the phalanx in the sagittal and/or transverse plane and then pin the phalanx to the metatarsal in that orientation. The clinician can then set the orientation of the phalanx in the frontal plane, e.g., by rotating the phalanx in the frontal plane about the pin. Once the orientation of the phalanx is set in the frontal plane, provisional and/or permanent fixation can be used to hold the moved position of the phalanx relative to the metatarsal for subsequent fusion.

According to some example implementations of the devices and techniques described herein, the metatarsal and phalanx separated by the MTP joint can be independently realigned relative to each other. For example, the position of the metatarsal in three-dimensional space may first be adjusted to a desired moved position and provisionally held in that moved position during subsequent realignment of the phalanx. The position of the phalanx can then be adjusted to a desired moved position in three-dimensional space (e.g., relative to the metatarsal that has already been realigned). With the metatarsal and proximal phalanx each independently realigned relative to each other, one or more fixation devices can be applied across and/or through the MTP joint to promote subsequent fusion of the bones. For example, one or more plates, screws, pins, and/or the like can be applied to permanently fixate the metatarsal to the phalanx and promote fusion of the bones at the MTP joint.

Through the stepwise adjustment of the orientation of the metatarsal and opposed phalanx, the position of each bone can be adjusted from an anatomically misaligned position toward a position of anatomical alignment.

In one example, a method is described that includes preparing a metatarsophalangeal joint for fusion. The method includes surgically accessing a metatarsophalangeal joint separating a metatarsal from an opposed proximal phalanx and preparing an end of the metatarsal and preparing an end of the opposed proximal phalanx. The method also includes moving the metatarsal in at least two planes to establish a moved position of the metatarsal and applying at least one bone fixation device across or through the metatarsophalangeal joint separating a metatarsal from an opposed proximal phalanx.

In another example, a method of preparing a metatarsophalangeal joint for fusion is described. The method includes surgically accessing a metatarsophalangeal joint separating a metatarsal from an opposed proximal phalanx, preparing an end of the metatarsal and preparing an end of the opposed proximal phalanx, and engaging a bone positioning guide with the metatarsal and a bone other than the metatarsal. The method also includes actuating the bone positioning guide and thereby moving the metatarsal in at least one plane to establish a moved position of the metatarsal and applying at least one bone fixation device across or through the metatarsophalangeal joint separating a metatarsal from an opposed proximal phalanx.

The details of one or more examples are set forth in the accompanying drawings and the description below. Other features, objects, and advantages will be apparent from the description and drawings, and from the claims.

BRIEF DESCRIPTION OF DRAWINGS

FIGS. 2A and 2B are top views of a foot showing a normal first metatarsal position and an example transverse plane misalignment position, respectively.

DETAILED DESCRIPTION

Figure 1B:
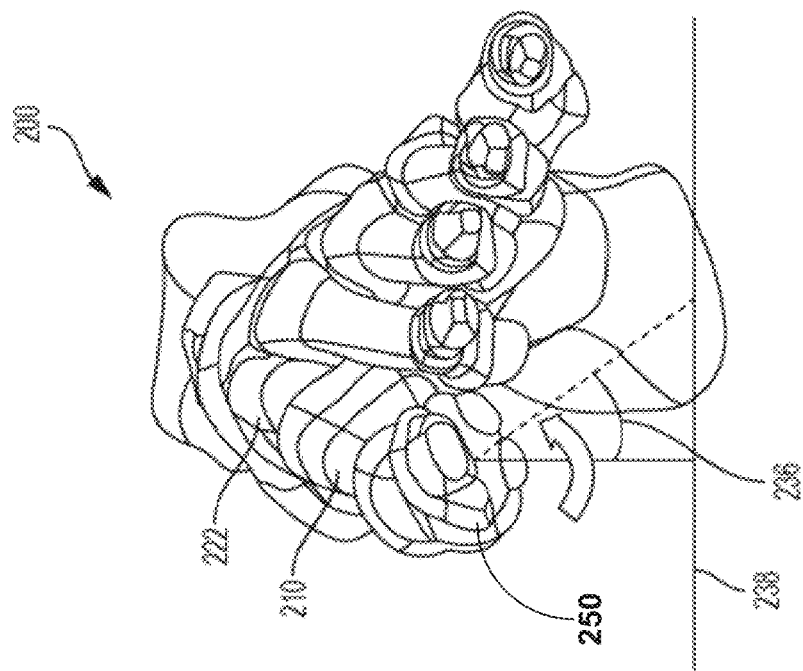
FIGS. 1A and 1B are front views of a foot showing a normal first metatarsal position and an example frontal plane rotational misalignment position, respectively.

In general, the present disclosure is directed to devices and techniques for preparing the metatarsophalangeal ("MTP") joint for fusion and realigning the metatarsal and phalanx separated by the joint. While a technique according to the disclosure can be performed on any MTP joint where a metatarsal is joined to an opposing proximal phalanx, in some implementations, the technique is performed on the first MTP joint where the first metatarsal joins the first proximal phalanx. During the procedure, a metatarsal may be separated from an opposing proximal phalanx at the MTP joint and both the metatarsal and opposing phalanx repositioned within one or more planes. After suitably repositioning the metatarsal and opposed proximal phalanx, the bone portions may be fixed to each using one or more fixation devices crossing the MTP joint. The end faces of the metatarsal and opposed proximal phalanx can be prepared prior to fixation, e.g., to promote realignment and/or subsequent fusion of the bones to each other.

Preparation and fusion of a metatarsal and phalanx may be performed according to the disclosure for a variety of clinical reasons and indications. Preparation and fusion of a metatarsal and proximal phalanx at the MTP joint may be performed to treat *Hallux rigidus*, *Hallux valgus*, and/or other bone and/or joint conditions.

*Hallux rigidus* is characterized as a degenerative arthritis of the MTP joint, particularly the first MTP joint. The cause of *Hallux rigidus* is often unclear. While arthritis can be caused by traumatic or iatrogenic injuries that directly cause damage to the articular cartilage of the MTP joint, most commonly the aetiology of *Hallux rigidus* is idiopathic. Patients may have family history and/or bilateral involvement leading to *Hallux rigidus*. As *Hallux rigidus* progresses, the normal coupling of the center of rotation of the proximal phalanx and metatarsal head may be disrupted, leading to eccentric gliding of proximal phalanx on the metatarsal head. Osteophytes may form preferentially on the dorsal surface. Further, while a normal first MTP motion may have approximately 75° of dorsiflexion and 35° of plantarflexion, patients with *Hallux rigidus* may typically exhibit a decreased range of motion, such as dorsiflexion less than 60°, such as less than 40°, less than 30°, or even less than 20°.

*Hallux valgus*, also referred to as *hallux* abducto *valgus*, is a complex progressive condition that is characterized by lateral deviation (*valgus*, abduction) of the *hallux* and medial deviation of the first metatarsophalangeal joint. *Hallux valgus* typically results in a progressive increase in the *hallux abductus* angle, the angle between the long axes of the first metatarsal and proximal phalanx in the transverse plane. An increase in the *Hallux abductus* angle may tend to laterally displace the plantar aponeurosis and tendons of the intrinsic and extrinsic muscles that cross over the first metatarsophalangeal joint from the metatarsal to the *hallux*. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the *crista* of the first metatarsal head.

While the techniques and devices are described herein particularly in connection with the first metatarsal and first proximal phalanx of the foot, the techniques and devices may be used on other adjacent bones separated by a joint in the hand or foot. For example, the techniques and devices may be performed on a different metatarsal (e.g., second, third, fourth, or fifth metatarsal) and its opposed proximal phalanx.

To further understand example techniques of the disclosure, the anatomy of the foot will first be described with respect to FIGS. 1-3 along with example misalignments that may occur and be corrected according to the present disclosure. As noted, a bone misalignment and/or MTP joint pain may be caused by *hallux valgus* (bunion), *Hallux rigidus*, a natural growth deformity, and/or other condition. The condition may present with a misalignment of one or more bones in the foot. Alternatively, the condition may present with evidence of arthritis at the MTP joint without visible misalignment of the bone forming the joint.

Figure 1A:
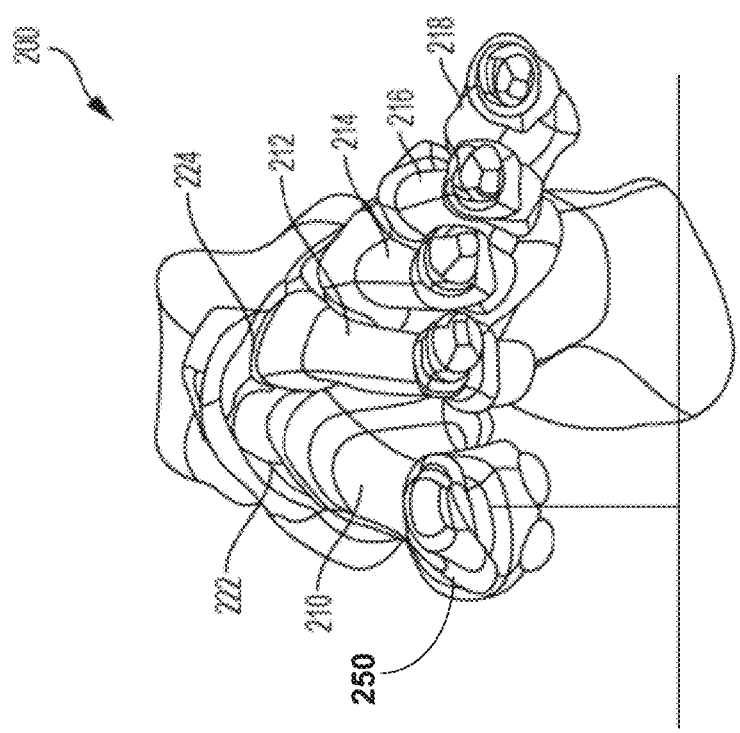
Figure 3B:
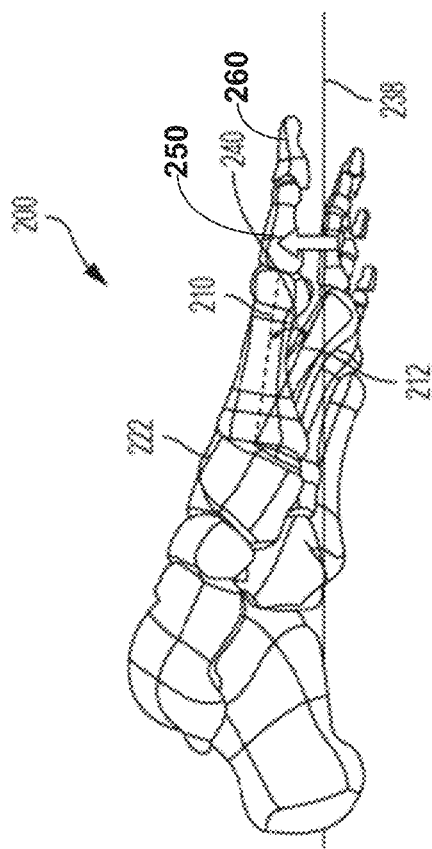
FIGS. 3A and 3B are side views of a foot showing a normal first metatarsal position and an example sagittal plane misalignment position, respectively.
Figure 3A:
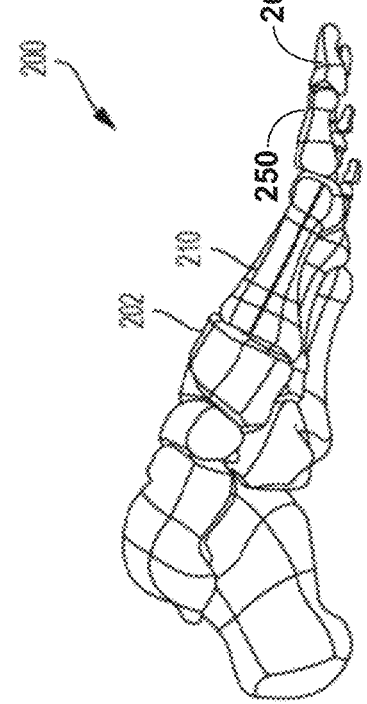

FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected. Further, a bone condition treated according to the disclosure may not present any of the example misalignments described with respect to FIGS. 1B, 2B, and 3B, and it should be appreciated that the disclosure is not limited in this respect.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. In particular, the first metatarsal 210 is connected distally to first proximal phalanx 250, the second metatarsal 212 is connected distally to second proximal phalanx 252, the third metatarsal 214 is connected distally to third proximal phalanx 254, the fourth metatarsal 216 is connected distally to fourth proximal phalanx 256, and the fifth metatarsal 218 is connected distally to fifth proximal phalanx 258. The joint 232 between a metatarsal and a corresponding opposed proximal phalanx is referred to as a metatarsophalangeal ("MTP") joint. The first MTP joint is labeled as joint 232 in FIG. 2A, although second, third, fourth, and fifth MTP joints are also illustrated in series adjacent to the first MTP joint.

The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and intersects an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

Bone positioning techniques and instruments can be useful to correct a misalignment of one or more bones, such as the metatarsal and opposed proximal phalanx, and/or promote fusion of the metatarsal and proximal phalanx across the MTP joint. In some applications, the technique involves releasing the MTP joint and preparing the end faces of the metatarsal and proximal phalanx for realignment relative to each other and/or fusion. The metatarsal undergoing the procedure may be moved in at least two planes, such as all three planes, to provide a moved position for fusing with the proximal phalanx. The proximal phalanx undergoing the procedure may also be moved in at least one plane, such as two or all three planes, relative to the metatarsal and/or an adjacent proximal phalanx. Once the metatarsal and proximal phalanx are appropriately repositioned, the metatarsal and proximal phalanx can be fixated to hold and maintain their relative positions to each other, e.g., and to promote fusion between the bones.

Figure 4:
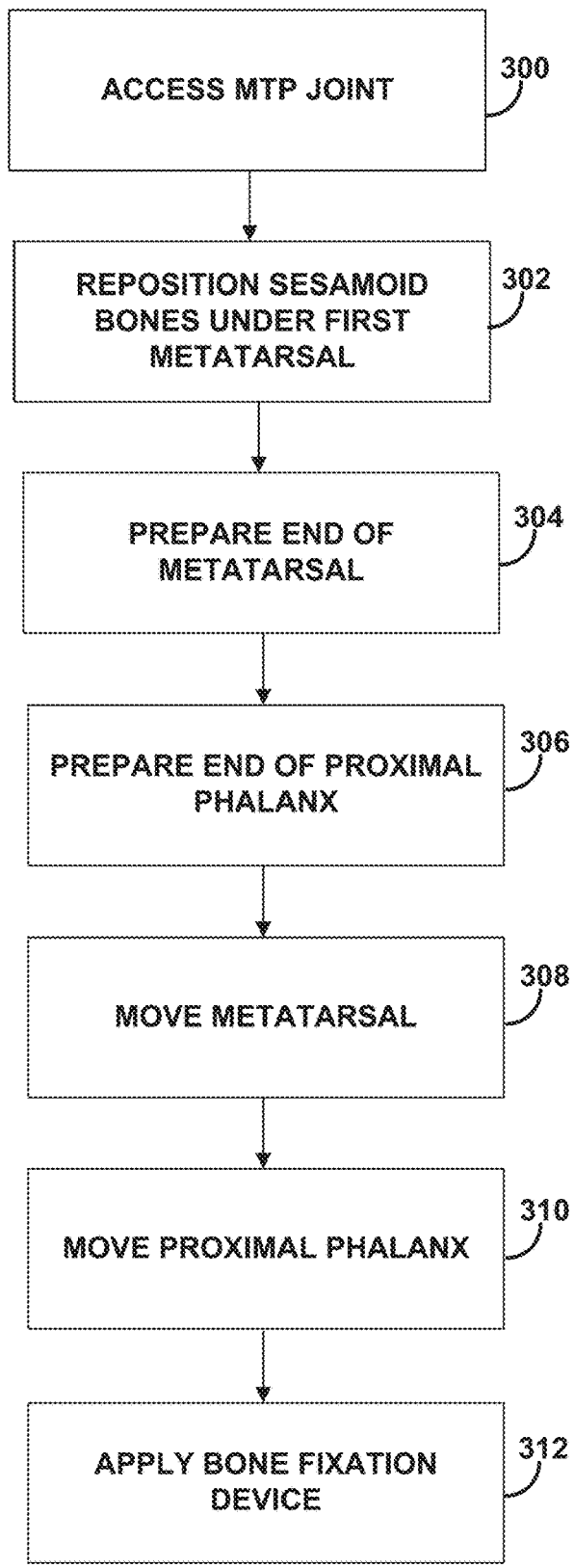
FIG. 4 is a flow diagram illustrating an example technique for preparing the MTP joint for fusion and realigning the metatarsal and proximal phalanx separated by the joint.

FIG. 4 is a flow diagram illustrating an example technique for preparing the MTP joint for fusion and realigning the metatarsal and proximal phalanx separated by the joint. The technique will be described with respect to first metatarsal 210 and first proximal phalanx 250, which are joined at the first MTP joint 232, although can be performed on other bones, as discussed above. For purposes of discussion, the technique of FIG. 4 will be discussed with respect to different example images of a procedure illustrated in FIGS. 5-16.

Figure 5:
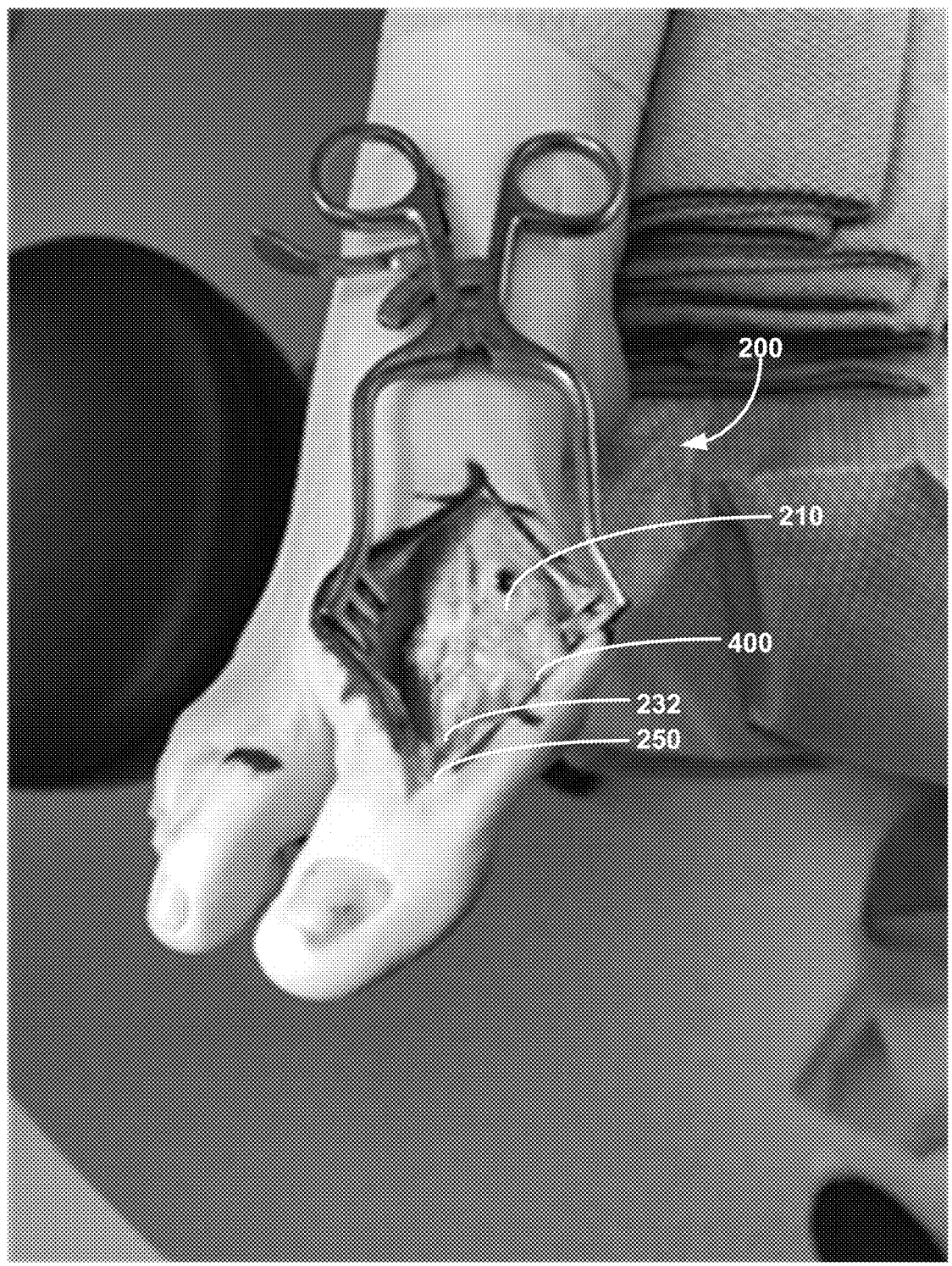
FIG. 5 is a perspective view of a foot showing example surgical access to the MTP joint.

FIG. 5 is a perspective view of a foot 200 showing example surgical access to the MTP joint. With reference to FIGS. 4 and 5, the example technique involves surgically accessing metatarsophalangeal joint 232 separating first metatarsal 210 from its opposed proximal phalanx 250 (300). To surgically access the joint, the patient may be placed in a supine position on the operating room table and general anesthesia or Monitored Anesthesia Care (MAC) administered. Hemostasis can be obtained by applying thigh tourniquet or mid-calf tourniquet. An incision 400 (FIG. 5) can be made on a dorsal side of the foot 200, such as a dorsal-medial side of the foot. For example, incision 400 may be made just medial to the extensor hallucis longus tendon centered over the first MTP joint 232. In some applications, a full thickness sub-periosteal dissection is carried out exposing the first MTP joint 232.

With the MTP joint 232 exposed, first metatarsal 210 may be separated from first proximal phalanx 250 at the joint. For example, first proximal phalanx 250 may be pushed plantarly, resulting in the end face of the first proximal phalanx separating from the end face of first metatarsal 210 to provide access to both end faces for subsequent operation. If needed, a soft tissue release performed at MTP joint 232 to help separate and release the metatarsal from the phalanx. When present, exuberant bony exostosis can be removed from the head (e.g., ed face) of the first metatarsal 210 and the base (e.g., end face) of the proximal phalanx 250.

Figure 6:
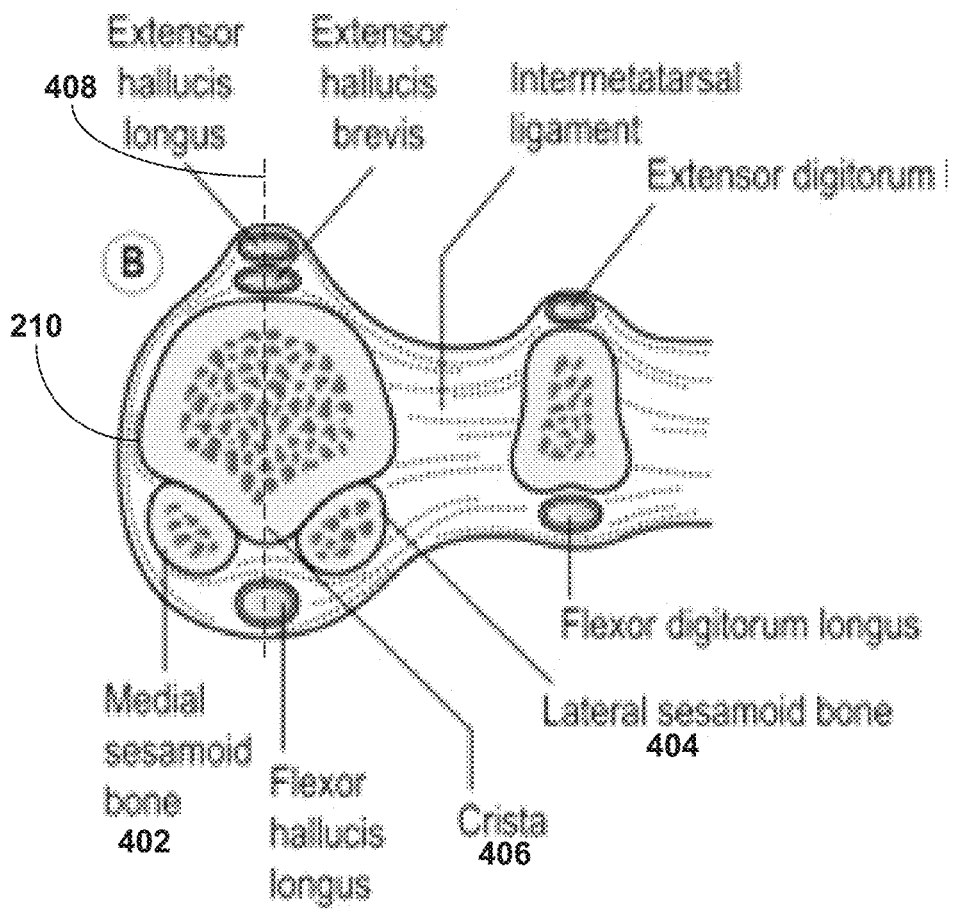
FIG. 6 is a side view of a first metatarsal and sesamoid complex showing the position of the sesamoid bones when in proper anatomical alignment.

In some examples of the technique of FIG. 4, the sesamoid complex is repositioned under the first metatarsal 210 (302). FIG. 6 is a side view of a first metatarsal and sesamoid complex showing the position of the sesamoid bones when in proper anatomical alignment. With reference to FIG. 6, the sesamoid bones 402, 404 are two bones positioned under the first metatarsal 210 when the bones and metatarsal are in proper anatomical realignment. The medial and lateral aspects of the plantar surface of the head of the first metatarsal 210 normally form shallow parallel grooves on either side of the central sagittal ridge called the *crista* 406. The medial and lateral sesamoid bones articulate with the medial and lateral grooves, respectively. The sesamoid bones slide forward in their respective grooves during extension (windlass action) and backward during flexion (reverse windlass action) of the first MTP joint 232 when in proper alignment.

Figure 7:
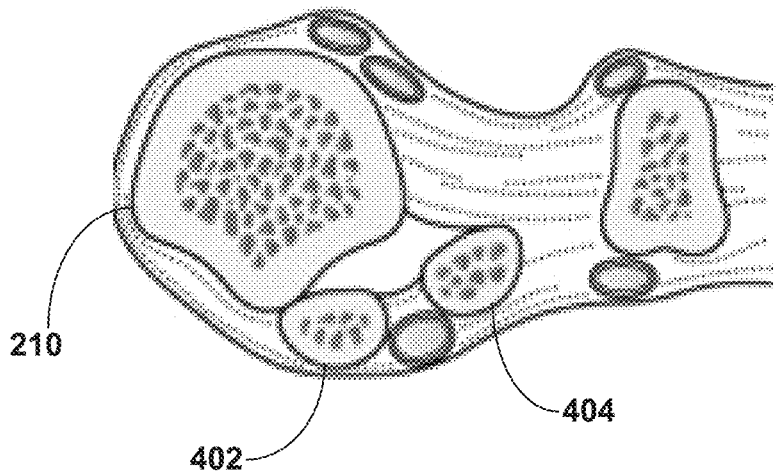
FIG. 7 is a side view of the first metatarsal and sesamoid complex from FIG. 6 showing an example anatomical misalignment of the sesamoid bones.

In the case of a misalignment, however, the sesamoid bones 402, 404 may be displaced (e.g., laterally) relative to the first MPT joint 232. FIG. 7 is a side view of the first metatarsal and sesamoid complex from FIG. 6 showing an example anatomical misalignment of the sesamoid bones. Displacement of the sesamoid bones 402, 404 may cause increased pressure between the medial sesamoid 402 and the *crista* 406 of the first metatarsal head 210 and decreased pressure between the lateral sesamoid 404 and the first metatarsal head.

In the technique of FIG. 4, the medial sesamoid bone 402 and the lateral sesamoid bone 404 may be repositioned on opposite sides of the sagittal plane 408. For example, the sesamoid bones 402, 404 may be positioned on opposite sides of the *crista* 406 within the respective parallel grooves formed by the head of the first metatarsal 210. To reposition the sesamoid bones, an instrument may be used to substantially fully release the capsular tissue at the MTP joint and for complete release of the sesamoids from the metatarsal. For example, a McGlamery elevator instrument may be used inserted (e.g., plantarly of the metatarsal) to release capsular tissue and to release the sesamoids, although a number of other instruments can be used instead of this particular device. The sesamoid bones 402, 404 may naturally realign upon being released from the first metatarsal 210, although manual manipulation or rotation (e.g., with or without the aid of a further instrument) may be used to assist realignment of the sesamoid bones.

Before or after the sesamoid bones are optionally repositioned in the technique of FIG. 4 (302), the end face of the first metatarsal 210 and/or the end face of the proximal phalanx 250 may be prepared (304, 306). Bone preparation can be useful, for instance, to facilitate contact between leading edges of metatarsal 210 and proximal phalanx 250. Preparation of the end faces may allow the two bones to be realigned relative to each other and/or to prepare the end faces to promote fusion between the end faces.

To prepare the end face of the first metatarsal 210 and/or the end face of the first proximal phalanx 250, a tissue removing instrument can be applied to the end face. Example tissue removing instruments that can be used include, but are not limited to, a saw, a rotary bur, a rongeur, a reamer, an osteotome, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of first metatarsal 210 and/or first proximal phalanx 250, the cutting may be performed freehand or with the aid of cutting guide having a guide surface positionable over the portion of bone to be cut. When using a cut guide, a cutting instrument can be inserted against the guide surface (e.g., between a slot define between two guide surfaces) to guide the cutting instrument for bone removal.

Figure 8:
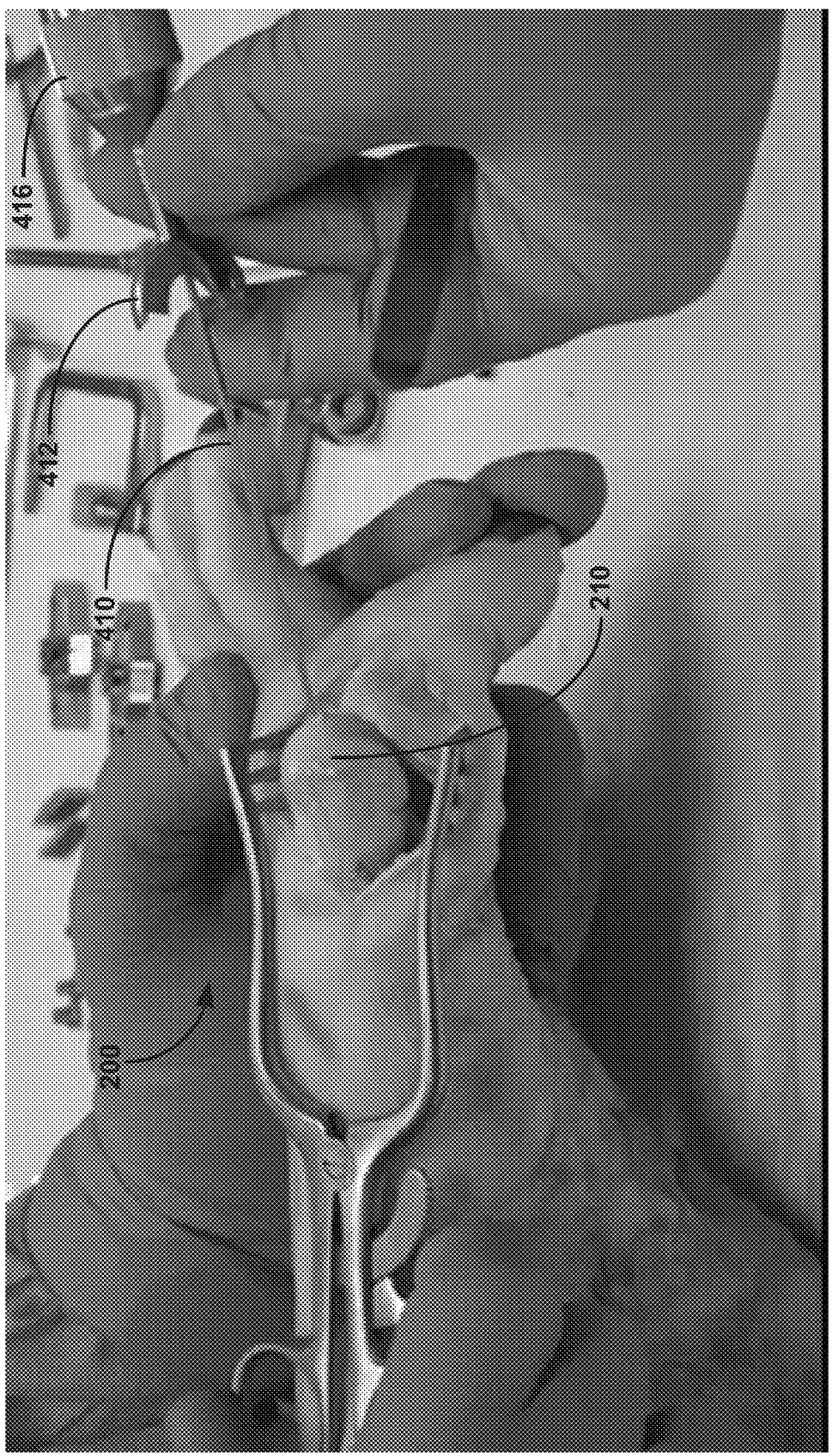
FIG. 8 is a perspective image of a foot illustrating an example preparation step performed on first metatarsal.

FIG. 8 is a perspective image of foot 200 illustrating an example preparation step performed on first metatarsal 210 (304). In the illustrated example, a guide pin 410 is inserted to project distally out of the end face of first metatarsal 210. A generally concave reamer 412 (e.g., a cone reamer) is advanced axially down the guide pin 412 and rotated using a rotary instrument 416 (e.g., drill). Reamer 412 (or other instrument, if a different surgical instrument is used) may denude the end face of the first metatarsal 210 of remaining cartilage down to the subchondral bone plate. In some examples, the end face of the first metatarsal 210 may be fenestrated in addition to or in lieu of one or more other end preparation steps, such as reaming the face with reamer 412.

The proximal phalanx 250 may be prepared using the same preparation technique or techniques performed on first metatarsal 210 or using a different preparation technique or techniques (306). In instances where the end face of the first metatarsal is prepared using a generally conically-shaped reamer 412, the end face of the first proximal phalanx 250 may be prepared using a corresponding generally convex reamer (e.g., a cup reamer). A guide pin may be inserted into the end face of the first proximal phalanx 250 and the convex reamer advanced down the guide pin and rotated using a rotary instrument. The reamer (or other instrument, if a different surgical instrument is used) may denude the end face of the proximal phalanx 250 of remaining cartilage down to the subchondral bone plate. In some examples, the end face of the proximal phalanx 250 may be fenestrated in addition to or in lieu of one or more other end preparation steps, such as reaming the face with the reamer.

In general, the specific order of the surgical steps performed in the technique of FIG. 4 may be varied without departing from the scope disclosure, and the example order illustrated in FIG. 4 it is merely for purposes of illustration. For example, the end face of the first metatarsal 210 may be prepared before or after the end face of the proximal phalanx 250 is prepared. Further, although FIG. 4 illustrates the end faces of the two bones as being prepared before moving either of the bones for realignment, one or both bones may be moved to a realigned position, as will be described below, before preparing an end face of one or both bones.

The technique of FIG. 4 involves moving the first metatarsal (e.g., relative to an adjacent metatarsal, such as a second metatarsal 212, and/or the first proximal phalanx 250) to establish a moved position of the metatarsal (308). In different examples, movement of the first metatarsal may be performed freehand (e.g., without the aid of a bone positioning device) and/or using instrumentation (e.g., a bone positioning device) to help facilitate repeatable repositioning outcomes.

When a bone positioning device is used, the bone positioning device may be any instrument that engages with the metatarsal being repositioned (e.g., first metatarsal 210) and a bone other than the metatarsal being repositioned. For example, the bone positioning device may engage with the metatarsal 210 on one side and another bone that acts as an anchor for the bone positioning device during actuation and corresponding movement of the metatarsal. The other bone used to anchor the bone positioning device may be another metatarsal (e.g., second metatarsal 212 or yet other metatarsal), a cuneiform such as medial cuneiform 222, or yet other anchoring bone. The bone positioning device may engage with the metatarsal being moved and the other bone through frictional contact without being fixedly coupled to the bone. Additionally or alternatively, a pin, screw, and/or other fixation element may be used to secure the bone positioning device to one or both bones.

In general, a bone positioning device may apply a force to a bone that causes the bone to move in at least one plane, such as the transverse plane and/or the frontal plane. In some examples, the force applied by the bone positioning device moves the metatarsal to which the force is applied in multiple planes, such as at least two planes or all three planes. For example, the bone positioning device may cause the first metatarsal 210 to be moved in the transverse plane to close the intermetatarsal angle and may also cause the metatarsal to rotate in the frontal plane.

Figure 9:
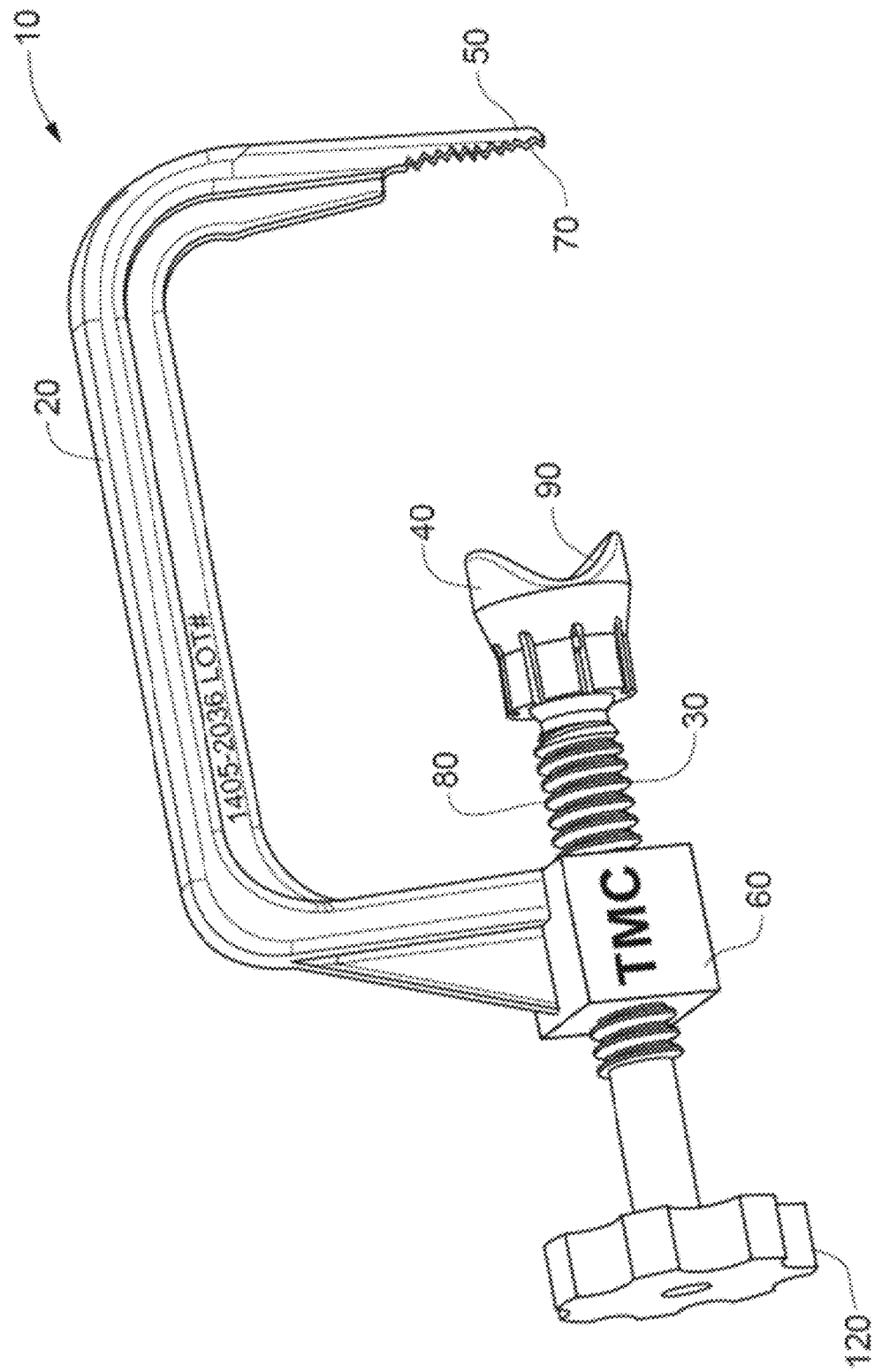
FIG. 9 is a perspective illustration of an example bone positioning device that can be used to move a metatarsal.

FIG. 9 is a perspective illustration of an example bone positioning device 10 that can be used to move first metatarsal 210. Additional details on bone positioning device 10 can be found in U.S. Pat. No. 9,936,994, titled "BONE POSITIONING GUIDE," and issued Apr. 10, 2018, the entire contents of which are incorporated herein by reference.

In the example of FIG. 9, a bone positioning device 10 (which may also be referred to as a bone positioning guide) includes a main body member 20, a shaft 30, a bone engagement member 40 connected to the shaft, and a tip 50 is connected to the main body member. In general, the main body member 20 can be sized and shaped to clear anatomy or other instrumentation (e.g., pins and guides) while positioned on a patient. As illustrated, the main body member 20 includes a generally C-shaped configuration with a first end 60 and a second end 70. In some embodiments, the main body is sized and configured to engage a metatarsal to be moved with bone engagement member 40 and another metatarsal that functions as an anchoring bone with tip 50. Although bone positioning device 10 is illustrated as being formed of two components, main body member 20 and shaft 30, the guide can be fabricated from more components (e.g., three, four, or more) that are joined together to form the guide.

Shaft 30 can be movably connected to the main body member 20 proximate its first end 60. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism, e.g., with or without a third device or by the clinician's hand pressure.

To move the ends of bone positioning device 10 relative to each other to move a bone engaged therewith, bone positioning device 10 can also include an actuator (e.g., a knob or a handle) 120 to actuate the mechanism. In the embodiment shown, the actuator can be useful for allowing a user to rotate the shaft with respect to the main body member 20. As shown, the actuator, shaft, and bone engagement member may include a cannulation to allow the placement of a fixation wire (e.g., K-wire) through these components and into contact with or through a bone engaged with the bone engagement member. For example, the fixation wire can be placed into the bone engaged with bone engagement member 40 to fix the position of the bone engagement member with respect to the bone. In another example, the fixation wire can be placed through the bone in contact with the bone engagement member and into an adjacent bone to maintain a bone position of the bone in contact with the bone engagement member and the adjacent bone.

While FIG. 9 illustrates one example configuration of a bone positioning device, the disclosure is not limited to the use of a bone positioning device with such an illustrated configuration. As one alternative example, instead of being configured to engage a metatarsal to be moved with bone engagement member 40 and another metatarsal with tip 50, the bone positioning device may be configured to extend from a metatarsal to be moved to a bone other than a metatarsal, such as a cuneiform to which the bone positioning device is anchored. As another example, a bone positioning device may utilize a tenaculum or tong structure to move one end engaged with the metatarsal relative to another anchoring bone. As a further example, a band, suture, and/or other interconnecting member may be attached to the metatarsal and a bone other than the metatarsal and then used to apply and/or translate a force to move the metatarsal.

In yet further examples, the clinician may use an instrument to apply a force to move the metatarsal without having the instrument simultaneously contact the metatarsal and a bone other than the metatarsal, e.g., in addition to or in lieu of using an bone positioning device that contacts both the metatarsal being moved and a bone other than the metatarsal. For example, the clinician may insert a pin into the metatarsal and manually manipulate the pin to control movement of the metatarsal. As another example, the clinician may insert one pin into a metatarsal and another pin into a bone other than the metatarsal (e.g., one into first metatarsal 210 and one into second metatarsal 212). The clinician may then squeeze the two pins together.

Independent of the configuration of the bone positioning device used (in instances where a bone positioning device is used), the bone positioning device may be configured to move the metatarsal being realigned in at least one plane (e.g., relative to the opposed proximal phalanx) and/or an adjacent metatarsal, such as at least two planes, or all three planes. The at least one plane can be the transverse plane, the frontal plane, and/or the sagittal plane. In some embodiments, actuation of the bone positioning device moves the metatarsal in at least the transverse plane to close the intermetatarsal angle ("IMA"), e.g., between first metatarsal 210 and second metatarsal 212. Actuation of the bone positioning device may reduce the IMA to an angle less than 12 degrees, such as less than 10 degrees, less than 8 degrees, less than 6 degrees, or less than 4 degrees.

In addition to or in lieu of moving the metatarsal in the transverse plane, actuation of the bone positioning device may realign the metatarsal in the frontal plane. A normal first metatarsal will be positioned such that its *crista* prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, the metatarsal is moved in the frontal plane to reducing the metatarsal rotation from about 4 degrees or more to less than 4 degrees (e.g., to about 0 to 2 degrees) by rotating the metatarsal.

In some implementations, such as when utilizing a bone positioning device 10 as illustrated in FIG. 9, actuation of the bone positioning device may simultaneously move the metatarsal in two planes to establish a moved position with respect to those planes. For example, actuating bone positioning device 10 may cause first metatarsal 210 to move in the transverse plane to close the IMA and in the frontal plane to move the *crista* prominence toward a 0 degree rotation angle.

When actuating the bone positioning device, the metatarsal may or may not also move in the sagittal plane (e.g., plantarly). For instance, in some implementations, actuating the bone positioning device causes the metatarsal to move in the transverse plane to close the IMA and the frontal plane to reduce the degree of rotation without any significant movement in the sagittal plane (e.g., such that there is less than 5 degrees of sagittal plane movement). This can maintain the sagittal plane declination of the first metatarsal while the position of the metatarsal is corrected in two other planes.

In some such example, the clinician may or may not perform a separate step to adjust the position of the metatarsal in the sagittal plane. For example, either before or after adjusting the position of the metatarsal in the transverse plane and/or frontal plane, the clinician may adjust the position of the metatarsal in the sagittal plane to help set a desired amount of dorsiflexion. For example, after moving first metatarsal 210 in the transverse plane and the frontal plane using bone positioning device 10, the clinician may manually grasp the metatarsal (e.g., by grasping the metatarsal directly, grasping a pin connected to the metatarsal, and/or with the use of a tong-type instrument) and move the first metatarsal in the sagittal plane. Bone positioning device 10 may continue to engage the metatarsal while the metatarsal is being moved in the sagittal plane, e.g., the help hold the moved position of the metatarsal in the frontal and/or transverse planes.

In some examples, the clinician moves first metatarsal 210 in the sagittal plane to help a declination angle (plantarflexion) for the first metatarsal that is substantially the same as the declination angle exhibited by an adjacent metatarsal (e.g., second metatarsal). The declination angle of the first metatarsal relative to the second metatarsal may be observed by taking a lateral X-ray image of foot 200. In some examples, the clinician moves first metatarsal 210 in the sagittal plane to set a declination angle relative to ground that is within approximately 5 degrees (plus or minus) of the declination angle of the second metatarsal, such as less than 3 degrees (plus or minus) different than the declination angle of the second metatarsal, or less than 2 degrees (plus or minus) different than the declination angle of the second metatarsal. In addition to or in lieu of moving the first metatarsal 210 relative to a declination angle of the second metatarsal 212, the clinician may move the metatarsal in the sagittal plane to establish a declination angle relative to ground, such as an angle ranging from 10 to 35 degrees with respect to ground, or from 20 to 25 degrees with respect to ground.

Figure 10:
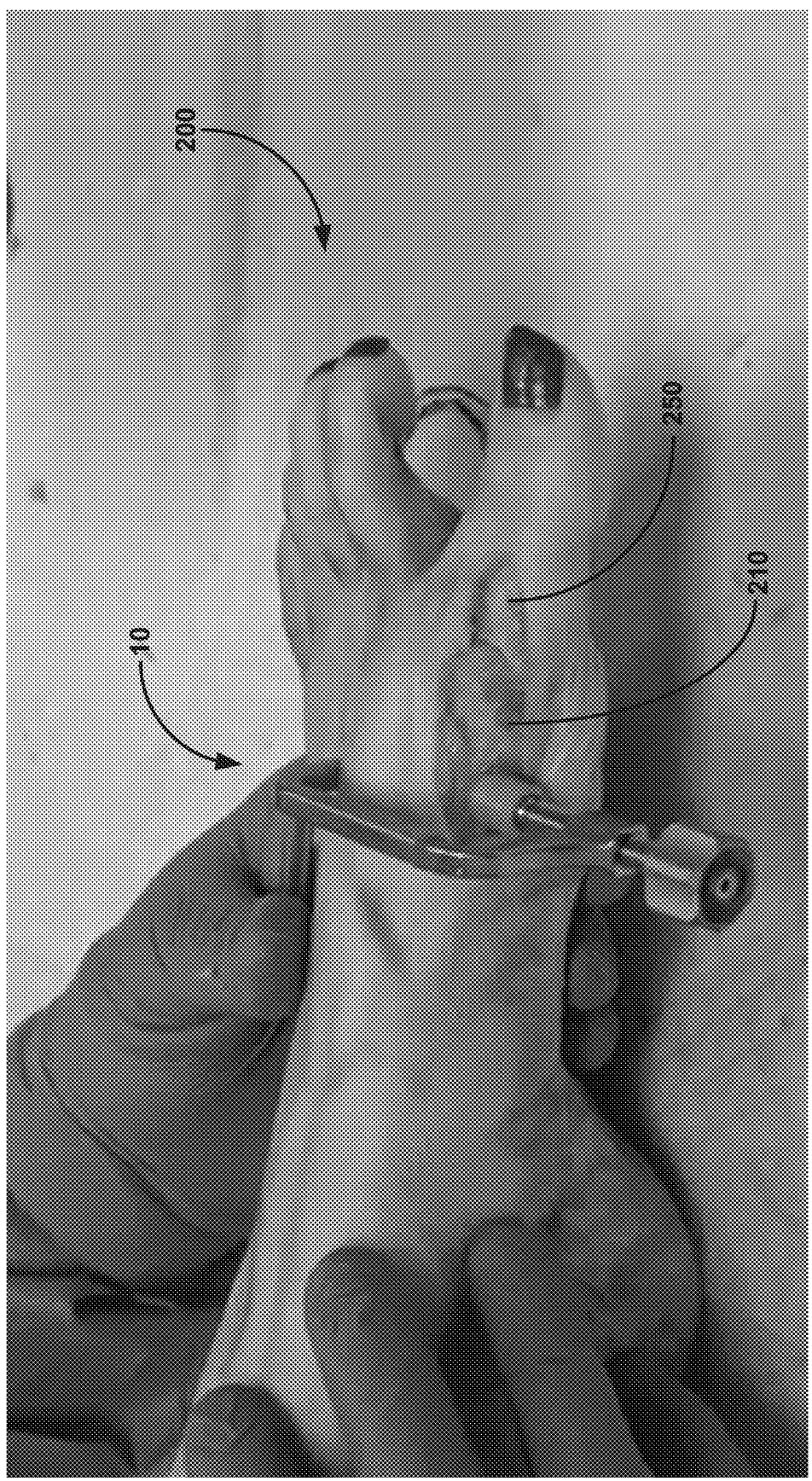
FIG. 10 is a perspective view of a foot showing the bone positioning device of FIG. 9 attached to the foot.

FIG. 10 is a perspective view of foot 200 showing bone positioning device 10 attached to the foot. In the example, the bone engagement member of bone positioning device 10 is placed in contact with first metatarsal 210, such as on the medial ridge of the first metatarsal. The tip 50 of bone positioning device 10 is placed through a stab incision on the lateral cortex of the second metatarsal 212. Actuation of bone positioning device 10 can cause a first ray deformity to be reduced on in the transverse and frontal planes.

If desired, a clinician may utilize a fulcrum between the metatarsal being moved and an adjacent metatarsal, e.g., to prevent compression of the metatarsals together during actuation of the bone positioning device. When used, the fulcrum may be inserted in the intermetatarsal space, e.g., between the distal head of the first metatarsal 210 and the adjacent second metatarsal 212. Additionally or alternatively, the fulcrum may be inserted between the proximal base of the metatarsal and the proximal base of an adjacent metatarsal (e.g., between the proximal base of the first and second metatarsals 210, 212), such as be making a stab incision at the base between the two metatarsals and inserting the fulcrum through the incision. Details on example fulcrum structures that may be used can be found in U.S. Pat. No. 10,342,590, issued Jul. 9, 2019 and titled "TARSAL-METATARSAL PROCEDURE UTILZING FULCRUM," the entire contents of which are incorporated herein by reference.

While the foregoing description has described the metatarsal as being moved in at least one plane with the aid of a bone positioning device, in other examples, the clinician may move the metatarsal by hand without the aid of a bone positioning device providing controlled movement of the metatarsal relative to another bone that the bone positioning device is also engaged with. In these alternative examples, the clinician may generally move the metatarsal in at least one plane, such as at least two planes (e.g., any two of the frontal, transverse, and sagittal planes), or all three planes. The clinician can move the metatarsal in one plane at a time, resulting in multiple different movements to achieve the multi-planar movement. Additionally or alternatively, the clinician may perform a single repositioning of the metatarsal in multiple planes. The clinician may move the metatarsal to any of the positions and/or angular ranges discussed above with respect to movement achieved when also using a bone positioning device.

Independent of whether the clinician utilizes a bone positioning device or moves the metatarsal without the aid of bone positioning device, the clinician may or may not insert two parallel reference pins to help visualize the bone movement. For example, prior to moving the metatarsal 210, the clinician may insert a first pin into the metatarsal and a second, parallel pin into the first proximal phalanx 250. The two pins may project out of the respective bones. As the bones are moved in three-dimensional space and/or relative to each other, the orientation of the two pins may shift out of parallel alignment. This may provide a visual guide to the clinician on the extent of relative movement between the bones.

In the example technique of FIG. 4, the first proximal phalanx 250 opposing the metatarsal 210 may be moved in at least one plane in addition to or in lieu of moving the metatarsal (310). For example, either before or after moving the first metatarsal 210 in at least one plane, the proximal phalanx 250 may be moved in at least one plane (e.g., any one of the frontal, transverse, and sagittal planes), such as at least two planes. For example, after moving the first metatarsal 210 in one, two, or three planes, the clinician may move the proximal phalanx in the sagittal plane and frontal plane relative to the moved metatarsal.

To help facilitate positioning of the proximal phalanx 250 relative to the first metatarsal 210, the clinician may provisionally fixate the position of the moved metatarsal. As one example, the clinician may insert a pin (e.g., a guide wire or K-wire) through the moved metatarsal and into another bone, such as an adjacent metatarsal (e.g., second metatarsal 212). When using bone positioning device 10, the pin can be inserted through the cannula in the actuator, through the first metatarsal, and into the second metatarsal. Alternatively, the bone positioning device used to apply a force to move the metatarsal may remain engaged with the bone (e.g., with actuator optionally locked), thereby functioning to hold the metatarsal in the moved position for subsequent realignment of the proximal phalanx 250. In still other examples, the moved metatarsal may not be provisionally held with a pin and/or instrumentation while adjusting the alignment of the proximal phalanx 250.

In one implementation, the clinician moves the proximal phalanx 250 and sets the position of the proximal phalanx using a pin extending generally parallel to the long axis of the proximal phalanx. For example, after moving the first metatarsal 210 to a desired position, the clinician may insert a pin (e.g., guide wire, K-wire) from the distal end of the hallux toward the moved metatarsal. The clinician can advance the pin in a distal to proximal direction through the distal phalanx 260 followed by the proximal phalanx 250 and into the end face of the first metatarsal 210. Prior to advancing the pin out of the proximal end face of the proximal phalanx 250 and into the distal end face of the first metatarsal 210, the clinician may move the proximal phalanx 250 (and attached distal phalanx 260) to a desired sagittal plane position and/or transverse plane position and/or frontal plane position. With the proximal phalanx 250 moved to a desired position in the sagittal plane, the clinician may advance the pin out of the proximal end face of the proximal phalanx 250 and into the distal end face of the first metatarsal 210, thereby provisionally fixating the proximal phalanx 250 to the first metatarsal 210 and holding the set sagittal plane position for the proximal phalanx. Additional details on example pin insertion and placement techniques may be found in U.S. Pat. No. 9,622,805, titled "BONE POSITIONING AND PREPARING GUIDE SYSTEMS AND METHODS," issued Apr. 18, 2017, the entire contents of which are incorporated herein by reference.

Figure 11:
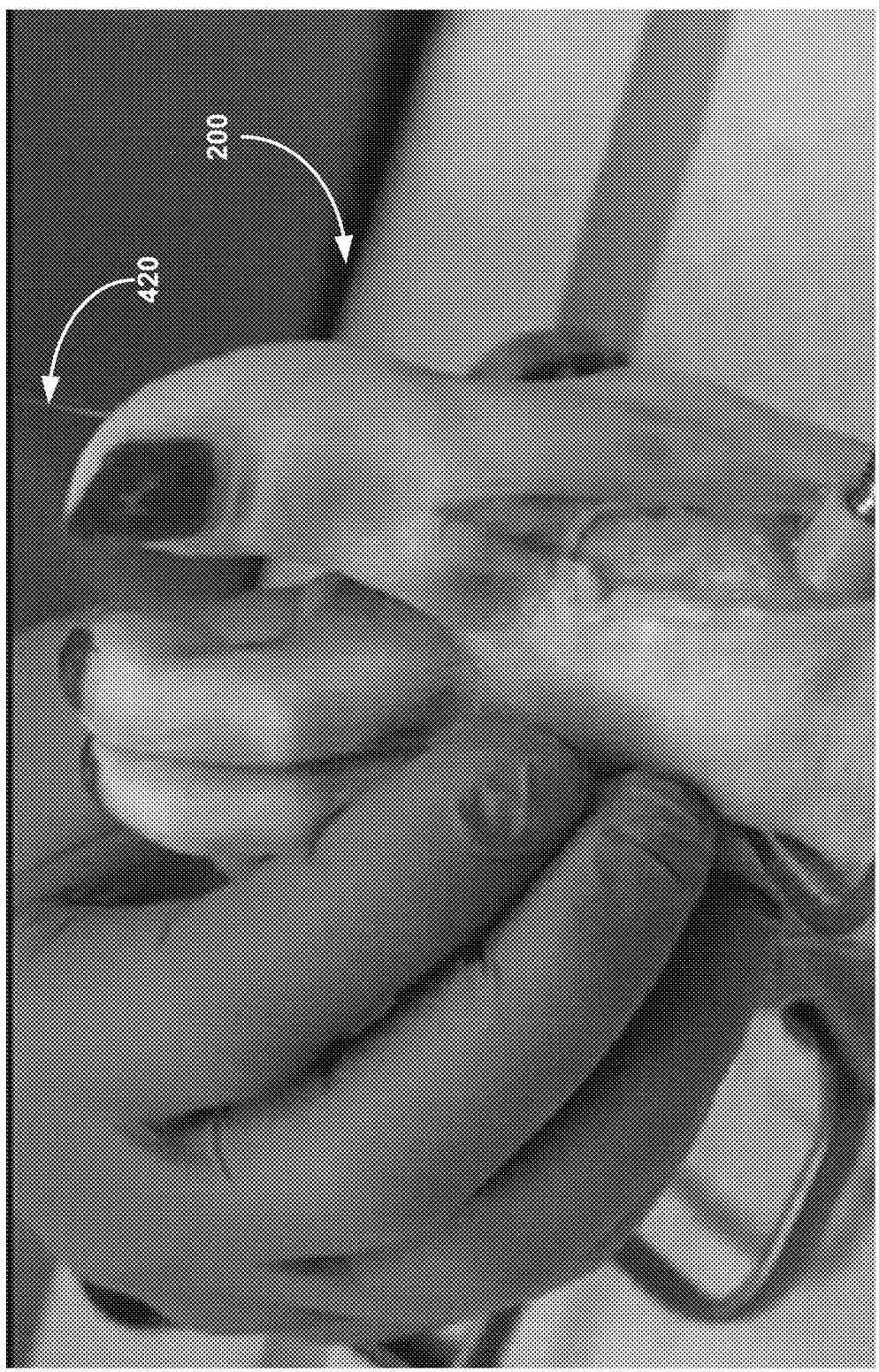
FIG. 11 is a perspective view of a foot showing an example pin inserted into the *hallux* of the foot and into the first metatarsal.
Figure 12:
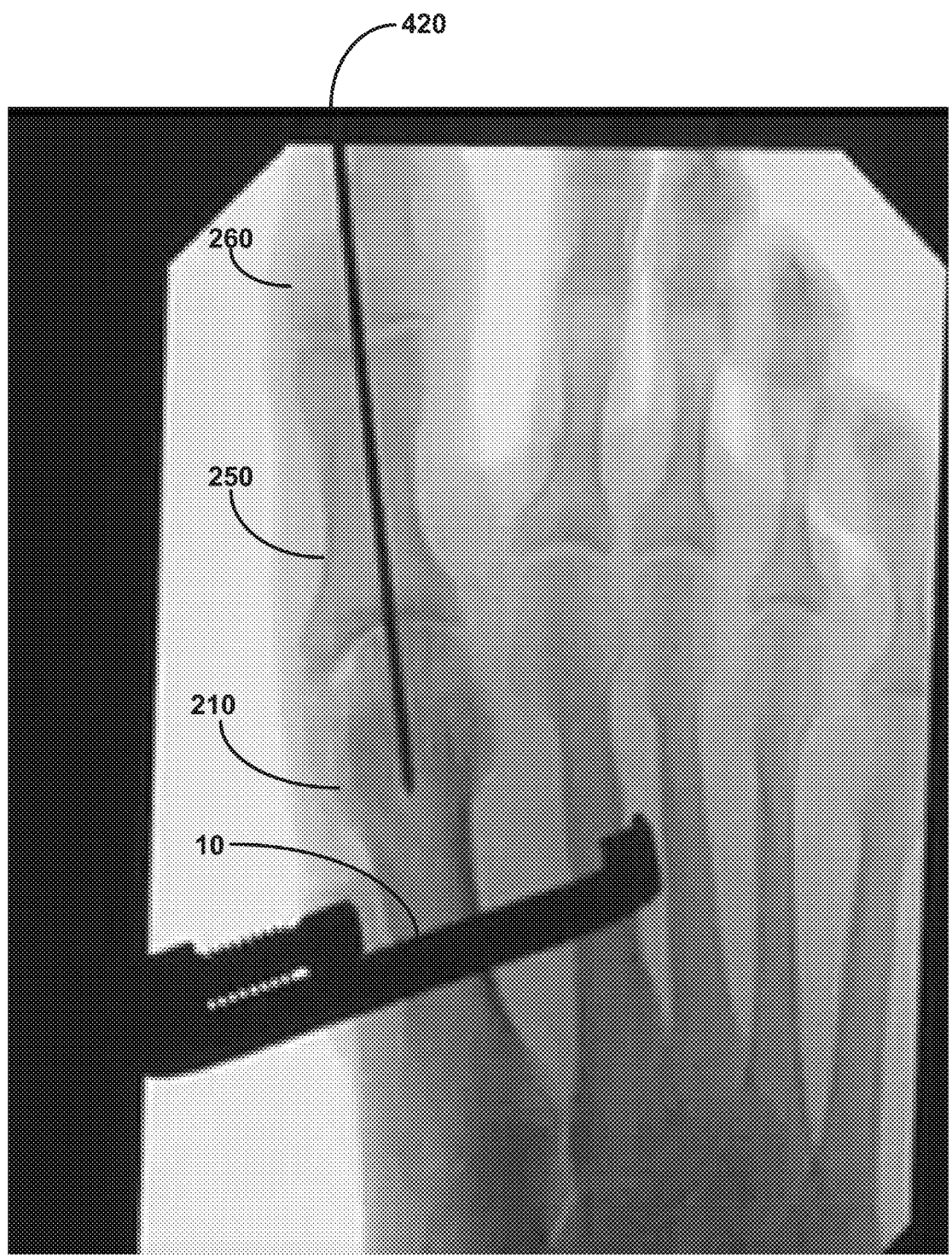
FIG. 12 is a fluoroscopic image of the foot of FIG. 11 taken in the dorsal to plantar direction.

FIG. 11 is a perspective view of foot 200 showing an example pin 420 inserted into the hallux of the foot and into the first metatarsal, e.g., to provisionally fixate the proximal phalanx relative to the metatarsal at a desired angular position in the sagittal plane. Pin 420 is shown projecting out the distal end of the hallux for visualization by the clinician. FIG. 12 is an X-ray of the foot 200 of FIG. 11 taken in the dorsal to plantar direction. The X-ray shows how pin 420 is inserted through distal phalanx 260, proximal phalanx 250, and into first metatarsal 210.

A variety of alternative provisional fixation instruments and/or techniques can be used in addition to or in lieu of a pin inserted proximally through the proximal phalanx 250 and into the first metatarsal 210. For example, a pin may be insert through the first metatarsal 210 into the proximal phalanx (e.g., from the dorsal side of the first metatarsal and advanced distally and plantarly across the MTP joint). As another example, a pin may be inserted into the proximal end of the proximal phalanx 250 to a depth sufficient to provide a small section of pin protruding out of the proximal end of the proximal phalanx. The pin may be positioned with distal end of the pin protruding out another side of the proximal phalanx. In either case, the proximal phalanx 250 can then be moved to a desired position with respect to the metatarsal 210. The pin can then be driven back through the proximal phalanx 250, e.g., by engaging the distal end of the pin with a driver mechanism, and into another bone, such as the opposed metatarsal 210.

In some examples, the clinician moves proximal phalanx 250 in the sagittal plane to help set a dorsiflexion angle measured relative to ground ranging from 0 degrees to 20 degrees, such as from approximately 5 degrees to approximately 10 degrees of dorsiflexion relative to the ground. The clinician may place the foot (or at least the metatarsal and hallux portion of the foot) on a planar surface, such a planar surface of a board or block. The clinician may then visualize and set the desired angle of proximal phalanx 250 in the sagittal plane relative to the planar surface. For example, the clinician may position the weight bearing surface of the foot in contact with the planar surface and view the position of the hallux interphalangeal joint, e.g., as pin 420 is being inserted and/or the position of the proximal phalanx is being adjusted in the sagittal plane. The clinician may set the plantar head of the proximal phalanx 250 at an angle of inclination relative where the weight bearing surface contacts the planar surface, e.g., within any of the foregoing angular ranges discussed above. In some examples, the clinician sets the plantar head of the proximal phalanx 250 to be positioned a distance less than 4 mm off of the planar surface contacted by the weight bearing surface of the foot, such as less than 3 mm, or a distance ranging from approximately 1 mm to approximately 2 mm.

In addition to or in lieu of positioning proximal phalanx 250 in the sagittal plane, the clinician be move the proximal phalanx in the transverse plane. The clinician may move the proximal phalanx to be substantially parallel to an adjacent proximal phalanx, e.g., such as by moving the first proximal phalanx 250 to be parallel to the second proximal phalanx 252.

With proximal phalanx 250 optionally provisionally fixated to first metatarsal 210 using pin 420, the clinician may move the proximal phalanx in the front plane to set a desired frontal plane position of the proximal phalanx. For example, the clinician can utilize pin 420 as a frontal plane axis of rotation and rotate proximal phalanx 250 about the pin to a desired frontal plane rotation position. The clinician may use the *hallux* and/or toenail as a reference for neutral or slight supination alignment of the *hallux*. The clinician may derotate proximal phalanx 250 until there is substantially no frontal plane rotation of the *hallux*.

With the proximal phalanx 250 moved to a desired position, the clinician may utilize intra-operative fluoroscopy to confirm the position of the first metatarsal 210 and/or proximal phalanx 250. For example, the clinician may generate fluoroscopic images in both the anterior-posterior view and lateral view to visualize the position of the bones in three-dimensional space. If needed, corrective repositioning of the metatarsal and/or proximal phalanx can be performed. Otherwise, if the clinician is satisfied with the positioning of the bones, the clinician may permanently fixate the MTP joint for fusion with the metatarsal and proximal phalanx in their relative moved positions.

Figure 13:
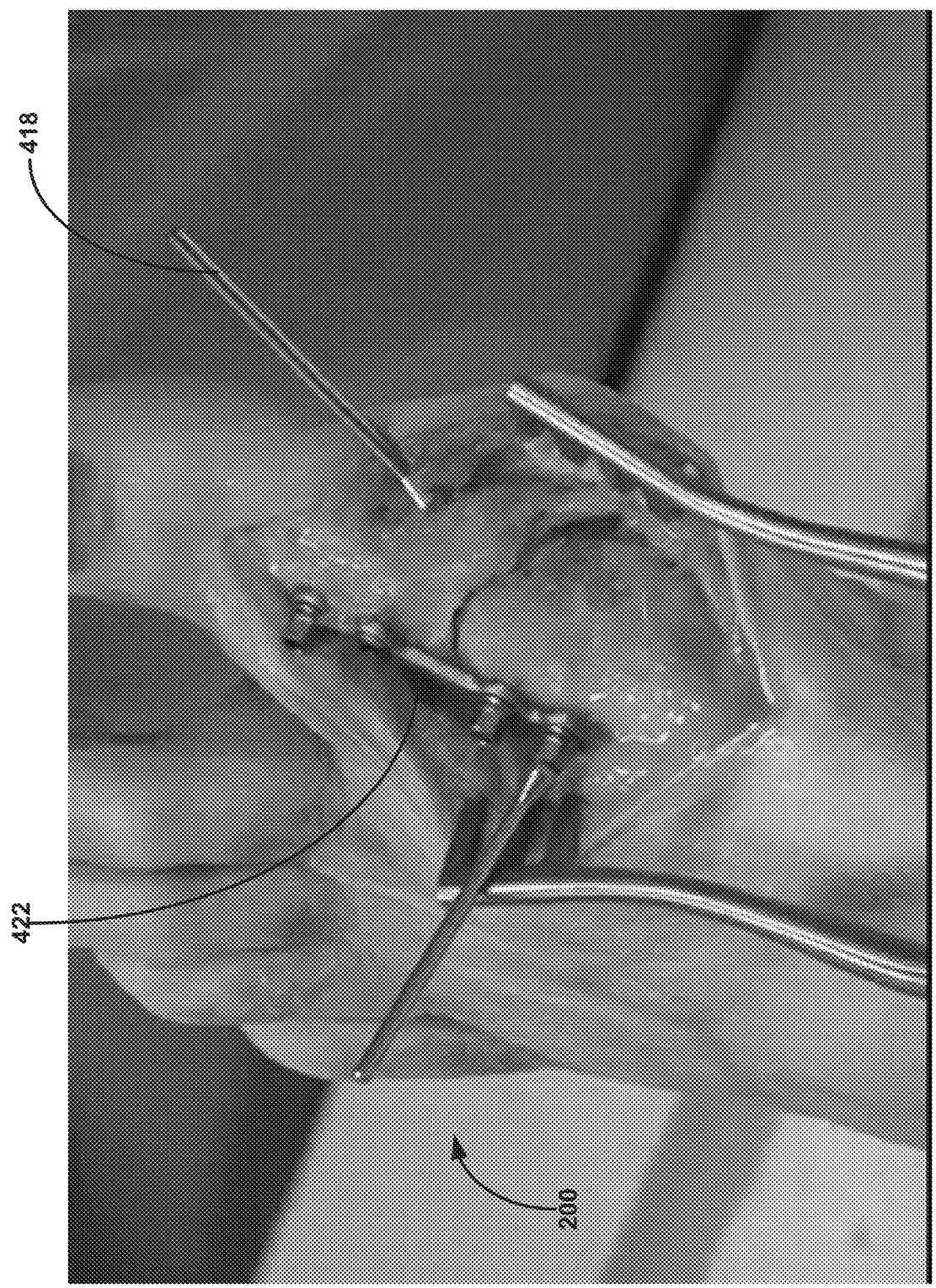
FIG. 13 is a perspective view of a foot showing a compression pin inserted through the proximal phalanx and into the first metatarsal along with an example bone plate.

In some examples, the clinician may compress the prepared end face of the proximal phalanx against the prepared end face of the metatarsal to facilitate fusion together prior to applying one or more permeant fixation devices. For example, the clinician use pin 420 to compress the proximal phalanx 250 to the first metatarsal 210, compressing the MTP joint. Additionally or alternatively, the clinician may insert a compression pin (e.g., a screw, a partially threaded olive wire, a K-wire, etc.) to compress across the MTP joint, e.g., by inserting the compression member from the dorsal-medial base of the proximal phalanx 250 across the first MTP joint 232 into the proximal-lateral first metatarsal shaft 210 for compression. When pin 420 is already inserted into the bones, the second pin may stabilize the frontal-plane correction of the phalanx. FIG. 13 is a perspective view of foot 200 showing a compression pin 418 inserted through the proximal phalanx and into the first metatarsal along with an example bone plate 422 being applied across the MTP joint.

To compress the prepared end of proximal phalanx 250 against the prepared end of first metatarsal 210 for fixation and fusion, a compressor instrument may optionally be used. FIGS. 15A-15D are illustrations of example surgical steps that may be performed to engage a compressor with a metatarsal and opposed proximal phalanx to facilitate compression. Some or all of the example steps of FIGS. 15A-15D up to compression may be performed before or after the end faces of the metatarsal and/or proximal phalanx are prepared and/or before or after realignment of the metatarsal and proximal phalanx. Further, while the example steps of FIGS. 15A-15D are described in connection with engaging a compressor device, the steps of FIGS. 15A-15C may additionally or alternatively be utilized to insert generally parallel guide pins into the metatarsal and opposed proximal phalanx, e.g., to help visualize realignment of one or both bone portions.

Figure 15A:
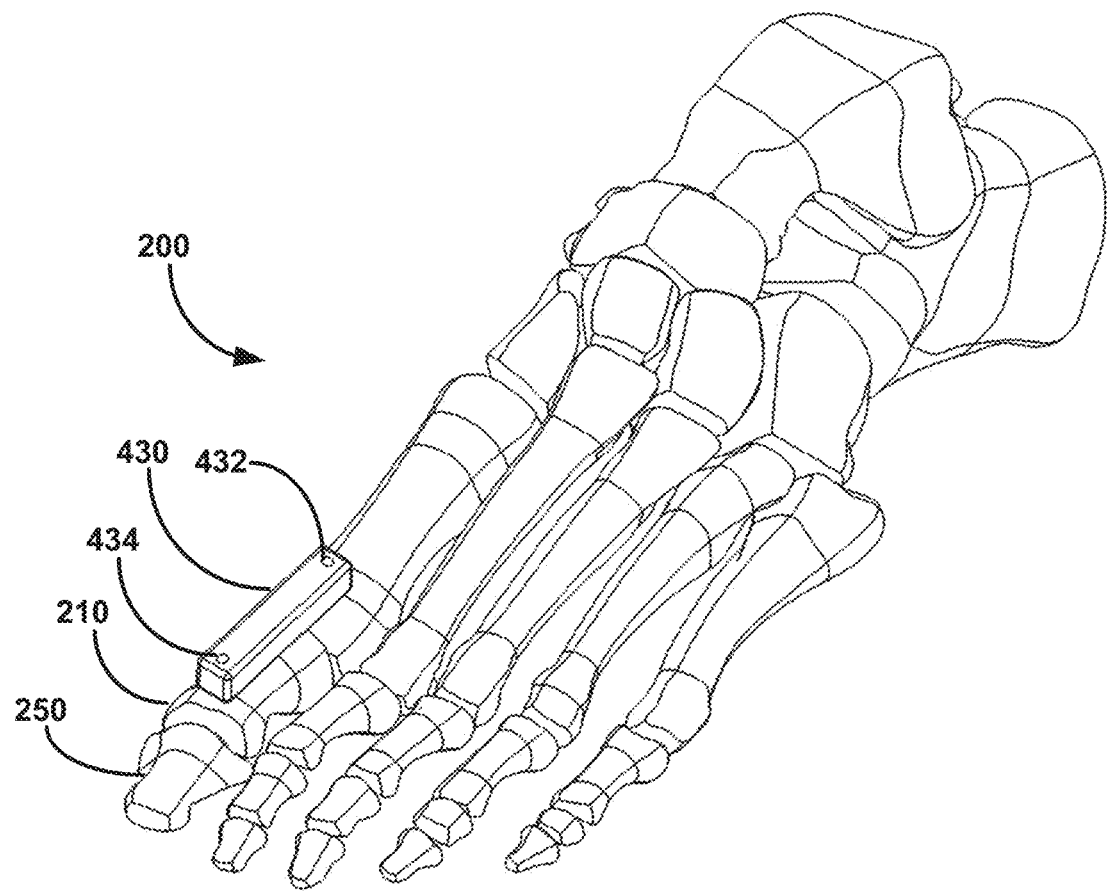
FIGS. 15A-15D are illustrations of example surgical steps that may be performed to engage a compressor with a metatarsal and opposed proximal phalanx to facilitate compression.

With reference to FIG. 15A, an optional guide 430 may be positioned on the first metatarsal 210 and/or opposed proximal phalanx 250. Guide 430 can define one or more apertures through which one or more corresponding pins can be insert. For example, guide 430 may cross the MTP joint and define at least one aperture 432 positioned over the first metatarsal 210 for receiving a pin and at least one aperture 434 positioned over the proximal phalanx for receiving a pin. The apertures may be oriented relative to each other to place the pins inserted therethrough at any desired orientation with respect to each other, such as generally parallel to each other and/or biased plantarly.

Figure 15B:
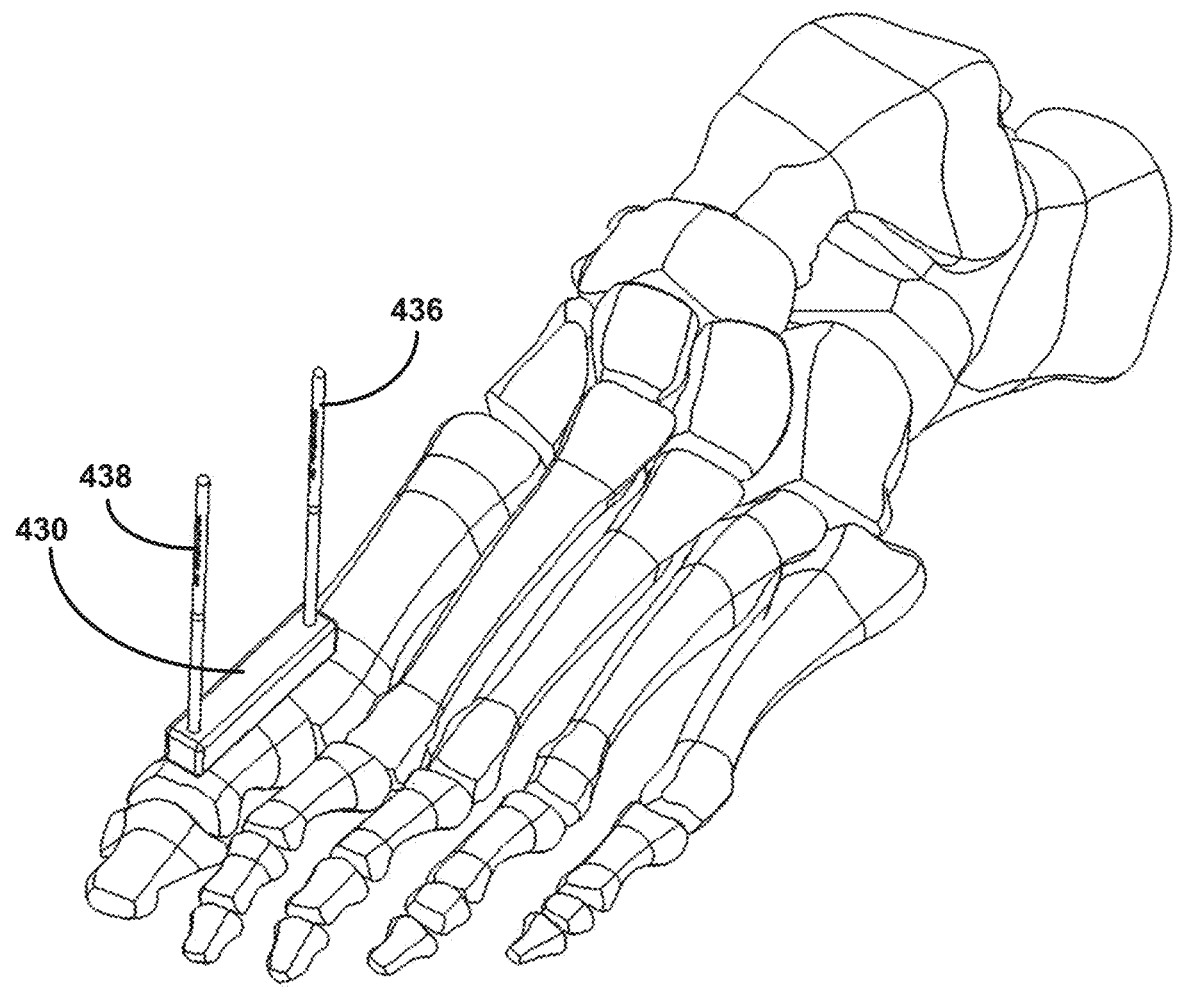
Figure 15C:
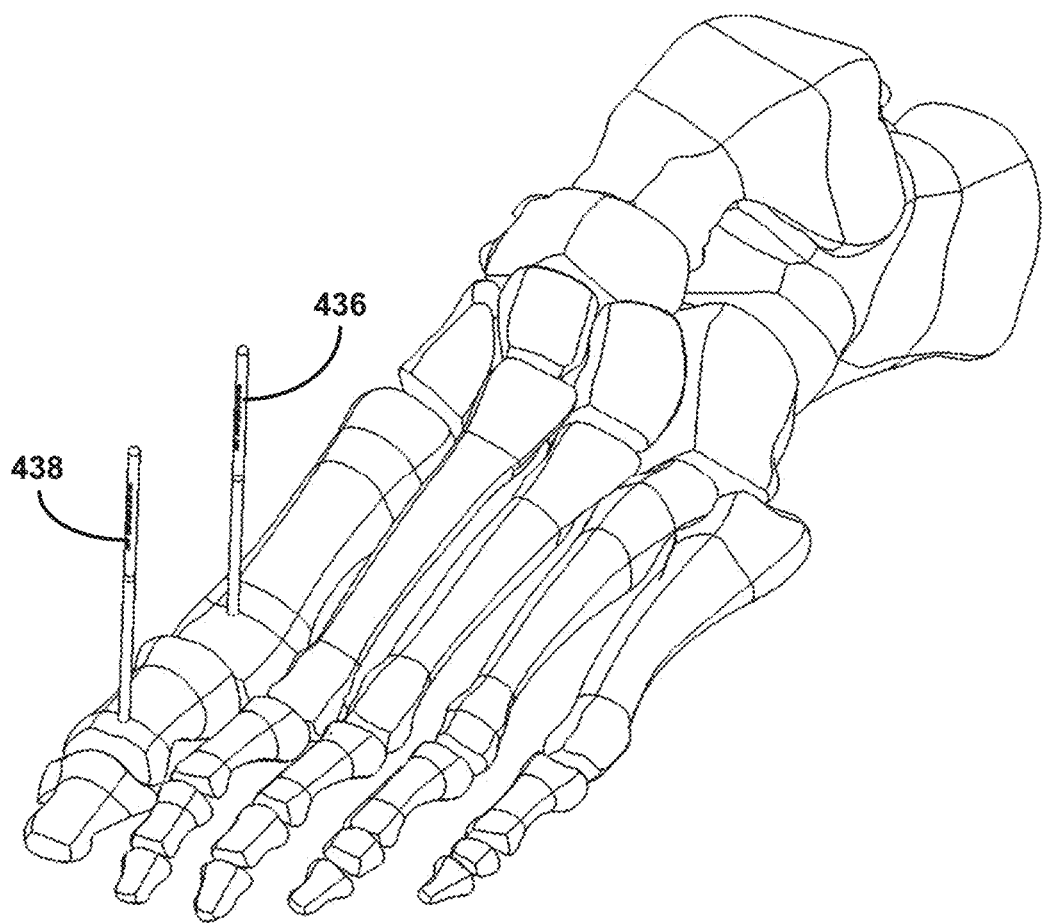

FIG. 15B illustrates a first pin 436 inserted through aperture 432 into first metatarsal 210 and a second pin 438 inserted through aperture 434 into proximal phalanx 250. In this example, the first and second pins 436, 438 extend dorsally and are generally parallel to each other. With the pin(s) positioned using optional guide 430, the guide may be removed as illustrated in FIG. 15C.

Figure 15D:
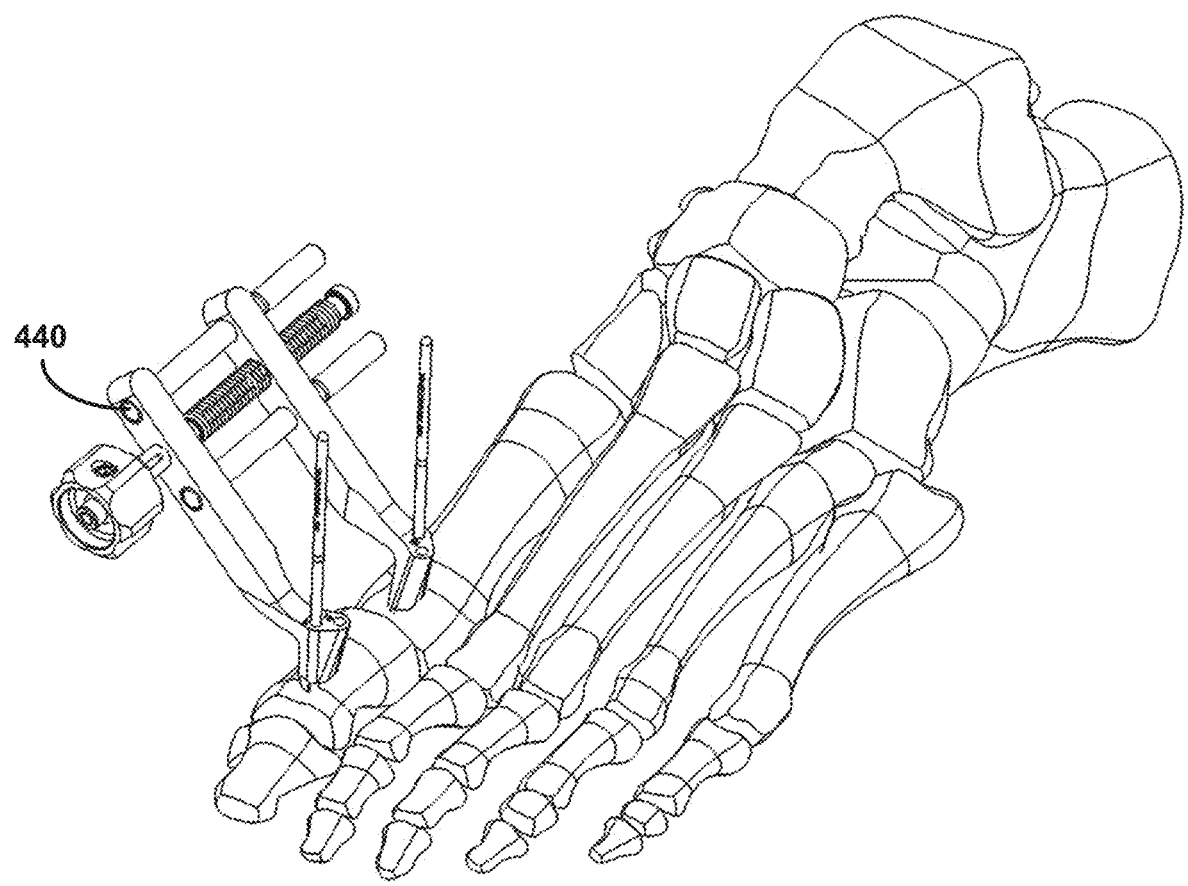

After suitably preparing and moving the first metatarsal 210 and proximal phalanx 250, the end face of the proximal phalanx can be compressed against the end face of the metatarsal. In some examples, an axial wire or pin may be placed to extend proximally out of the end face of the proximal phalanx. When used, the proximal phalanx may slide along the wire or pin during compression. In either case, a compressor instrument 440 may be installed on the first pin 436 and the second pin 438 and then engaged to compress the bones attached to the pins together, as illustrated in FIG. 15D. Additional details on compressor instrumentation that may be used can be found in US Patent Publication 2020/0015856, filed Jul. 11, 2019 and titled "COMPRESSOR-DISTRACTOR FOR ANGULARLY REALIGNING BONE PORTIONS," the entire contents of which are incorporated herein by reference.

With reference to FIG. 4, the example technique includes applying at least one bone fixation device across or through the MTP joint separating the metatarsal from the opposed proximal phalanx (312). Any one or more bone fixation devices can be used including, but not limited to, a compressing bone screw, a bone plate, a bone staple, an external fixator, and/or an intramedullary implant. The bone fixation device may be secured on one side to the metatarsal, bridge the MTP joint, and be secured on an opposite side to the proximal phalanx.

Figure 14:
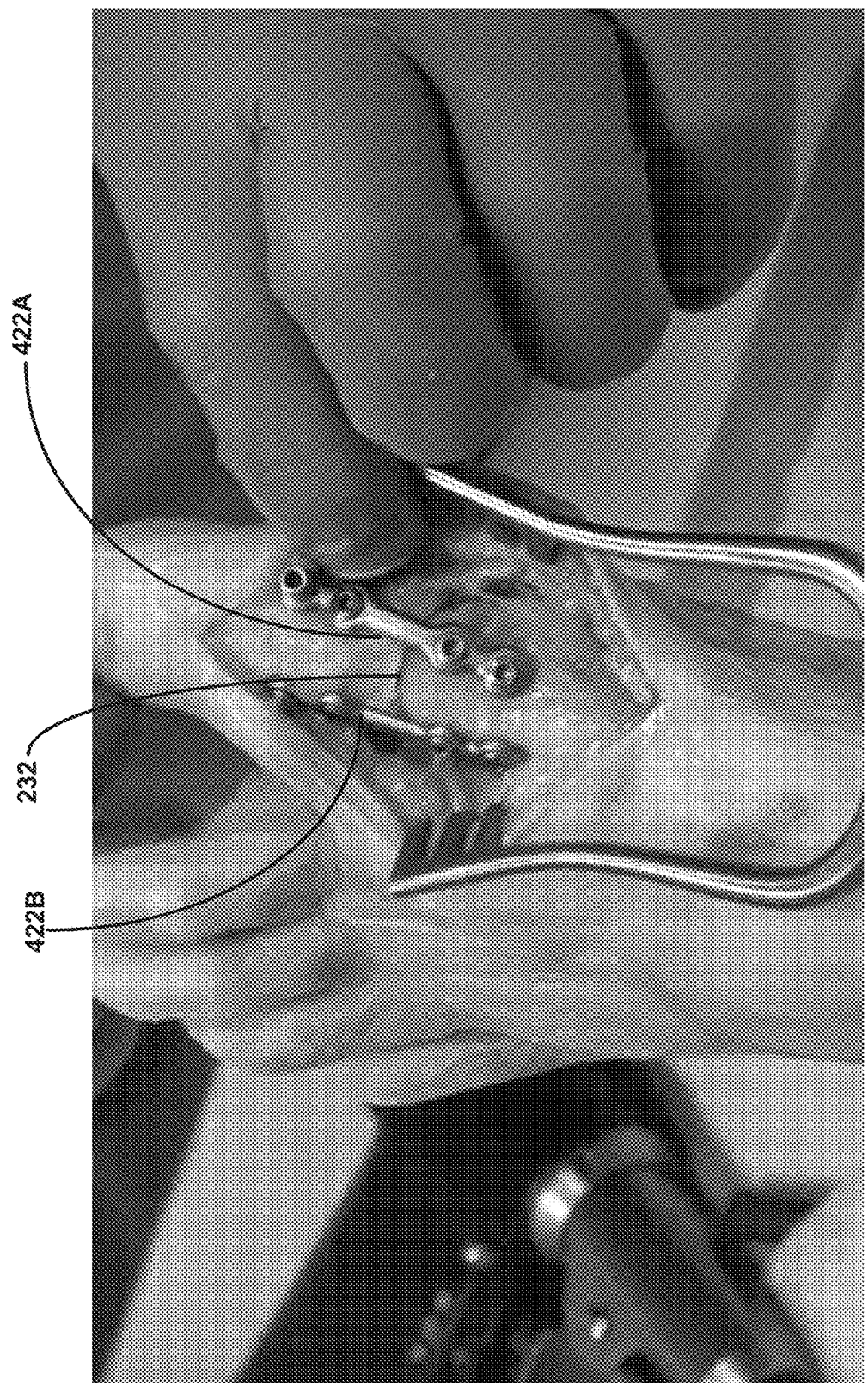
FIG. 14 is a perspective view of a foot showing example bi-planar bone plates.

In one example, two bone plates may be placed across the MTP joint to provide bi-planar plating. For example, a first bone plate may be positioned on a dorsal-medial side of the metatarsal and proximal phalanx. A second bone plate may be positioned on a medial-plantar side of the metatarsal and the proximal phalanx. Independent of the number or configuration of bone plates, the plates may be applied with the insertion of bone screws. FIG. 14 is a perspective view of foot 200 showing example bi-planar bone plates 422A, 422B applied across the MTP joint to allow the metatarsal to fuse to the proximal phalanx during subsequent recovery.

Figure 16:
FIGS. 16 and 17 are pre- and post-operative fluoroscopic images of a foot showing example bone realignment according to the techniques of the present disclosure.
Figure 17:

FIGS. 16 and 17 are pre- and post-operative fluoroscopic images of a foot showing example bone realignment according to the techniques of the present disclosure.

Various examples have been described. These and other examples are within the scope of the following claims.

The invention claimed is:

1. A method of preparing a metatarsophalangeal joint for fusion, the method comprising:
surgically accessing a metatarsophalangeal joint separating a metatarsal from an opposed proximal phalanx;
preparing an end of the metatarsal and preparing an end of the opposed proximal phalanx;
moving the metatarsal in at least two planes to establish a moved position of the metatarsal;
applying at least one bone fixation device at least one of across and through the metatarsophalangeal joint separating the metatarsal from the opposed proximal phalanx.

2. The method of claim 1, wherein moving the metatarsal in at least two planes comprises moving the metatarsal in three planes.

3. The method of claim 2, wherein moving the metatarsal comprises:
moving the metatarsal in a frontal plane and a transverse plane, and
after moving the metatarsal in the frontal plane and the transverse plane, moving the metatarsal in a sagittal plane.

4. The method of claim 1, wherein moving the metatarsal in at least two planes comprises reducing an angle between the metatarsal and an adjacent metatarsal to less than 12 degrees.

5. The method of claim 1, wherein moving the metatarsal comprises moving the metatarsal after preparing the end of the metatarsal and after preparing the end of the opposed phalanx.

6. The method of claim 1, further comprising moving the opposed proximal phalanx relative to the metatarsal in at least a sagittal plane.

7. The method of claim 6, further comprising moving the opposed proximal phalanx in a frontal plane.

8. The method of claim 7, further comprising inserting a pin through the opposed proximal phalanx and into the metatarsal, wherein moving the opposed proximal phalanx in the frontal plane comprises rotating the proximal phalanx about the pin.

9. The method of claim 1, further comprising repositioning a medial sesamoid bone associated with the metatarsal and a lateral sesamoid bone associated with the metatarsal on opposite sides of a sagittal plane.

10. The method of claim 9, wherein repositioning the medial sesamoid bone and the lateral sesamoid bone comprises releasing the medial sesamoid bone and the lateral sesamoid bone with an instrument and repositioning the medial sesamoid bone and the lateral sesamoid bone prior to moving the metatarsal in the at least two planes.

11. The method of claim 1, further comprising engaging a bone positioning guide with the metatarsal and a bone other than the metatarsal, wherein moving the metatarsal in the at least two planes comprises actuating the bone positioning guide and thereby moving the metatarsal in at least one of the two planes using the bone positioning guide.

12. The method of claim 11, wherein actuating the bone positioning guide comprises actuating the bone positioning guide and thereby moving the metatarsal in at least a frontal plane and a transverse plane.

13. The method of claim 11, wherein engaging the bone positioning guide with the metatarsal and the bone other than the metatarsal comprises engaging the bone positioning guide with the metatarsal and another metatarsal.

14. The method of claim 11, wherein the bone positioning guide comprises:
a first end configured to engage the metatarsal and a second end configured to engage the bone other than the metatarsal, and
a mechanism configured to move the first end and the second end toward each other.

15. The method of claim 14, wherein the mechanism comprises at least one of a ratchet and a threaded shaft.

16. The method of claim 1, wherein preparing the end of the metatarsal and preparing the end of the opposed proximal phalanx each comprises removing cartilage down to subchondral bone.

17. The method of claim 1, wherein:
preparing the end of the metatarsal comprises reaming the end of the metatarsal with a generally conical-shaped reamer, and
preparing the end of the opposed proximal phalanx comprises reaming the end of the opposed phalanx with a generally cone-shaped reamer.

18. The method of claim 1, further comprising, prior to applying the at least one bone fixation device, provisionally fixing the moved position of the metatarsal.

19. The method of claim 18, wherein provisionally fixing the moved position of the metatarsal comprises inserting a pin into the metatarsal and a bone other than the metatarsal.

20. The method of claim 19, wherein inserting the pin into the metatarsal and the bone other than the metatarsal comprises inserting the pin through the opposed proximal phalanx and into the metatarsal.

21. The method of claim 19, wherein inserting the pin into the metatarsal and the bone other than the metatarsal comprises inserting the pin into the metatarsal and an adjacent metatarsal.

22. The method of claim 1, further comprising, prior to applying the at least one bone fixation device, compressing the opposed proximal phalanx and the metatarsal together across the metatarsophalangeal joint.

23. The method of claim 1, wherein the at least one bone fixation device comprises at least one of a bone plate, a pin, a screw, and a staple.

24. The method of claim 1, wherein the at least one bone fixation device comprises:
a first plate, and
at least one of a second plate and an intramedullary screw.

25. A method of preparing a metatarsophalangeal joint for fusion, the method comprising:
surgically accessing a metatarsophalangeal joint separating a metatarsal from an opposed proximal phalanx;
preparing an end of the metatarsal and preparing an end of the opposed proximal phalanx;
engaging a bone positioning guide with the metatarsal and a bone other than the metatarsal;
actuating the bone positioning guide and thereby moving the metatarsal in at least one plane to establish a moved position of the metatarsal;
applying at least one bone fixation device at least one of across and through the metatarsophalangeal joint separating a metatarsal from an opposed proximal phalanx.

* * * * *